United States Patent [19]
Hoerrmann

[11] Patent Number: 6,066,665
[45] Date of Patent: May 23, 2000

[54] COMBINATION OF CIS-4-HYDROXY-L-PROLINE AND N-METHYL-CIS-4-HYDROXY-L-PROLINE FOR USE AS A THERAPEUTIC AGENT, IN PARTICULAR IN CANCER TREATMENT

[76] Inventor: Wilhelm Hoerrmann, Staltacherstrasse 34, Iffeldorf D-82393, Germany

[21] Appl. No.: 09/142,478

[22] PCT Filed: Mar. 11, 1997

[86] PCT No.: PCT/DE97/00486

§ 371 Date: Sep. 9, 1998

§ 102(e) Date: Sep. 9, 1998

[87] PCT Pub. No.: WO97/33578

PCT Pub. Date: Sep. 18, 1997

[30] Foreign Application Priority Data

Mar. 11, 1996 [DE] Germany .......................... 196 09 454

[51] Int. Cl.[7] .................................................. A61K 31/40
[52] U.S. Cl. ............................................................ 514/423
[58] Field of Search ............................................. 514/423

[56] References Cited

U.S. PATENT DOCUMENTS 5,665,371  9/1997  Hoerrmann .............................. 424/423

FOREIGN PATENT DOCUMENTS

| 0223850 | 6/1987 | European Pat. Off. . |
| 3538619 | 5/1986 | Germany . |
| 2171302 | 8/1986 | United Kingdom . |

OTHER PUBLICATIONS

Journal of the National Cancer Institute, vol. 75, No. 2, 1985, pp. 353–359, Klohs et al, "Collagen–Production Inhibitors . . . ".

Biology of Reproduction, vol. 33, No. 1, 1985, pp. 213–227, Thornton et al, "Collagen and the Proliferation and . . . ".

Cancer Research, vol. 41, No. 7, 1981, pp. 2855–2862, Lewko et al, "Sensitivity of N–Nitrosomethylurea–induced Mammary . . . ".

*Primary Examiner*—Jerome D. Goldberg
*Attorney, Agent, or Firm*—Jacobson, Price, Holman & Stern, PLLC

[57] ABSTRACT

The disclosure relates to a combination of cis-4-hydroxy-L-proline and n-methyl-cis-4-hydroxy-L-proline for use as a therapeutic agent, in particular in cancer treatment. Also disclosed is the use of the individual substances for treating hormone-sensitive prostate cancer.

15 Claims, 27 Drawing Sheets

RENAL CARCINOMA
CELL LINE: KTCTL2
CONCENTRATION: 100 μg/mL

HIGHLY DIFFERENTIATED PAPILLARY
BLADDER CARCINOMA

CELL LINE: RT4
MEDICAMENT: N-METHYL-CIS-4-HYDROXY-L-PROLINE

HIGHLY DIFFERENTIATED PAPILLARY
BLADDER CARCINOMA

CELL LINE: RT4
MEDICAMENT: N-METHYL-CIS-4-HYDROXY-L-PROLINE + CIS-4-HYDROXY-L-PROLINE

ESTROGEN-SENSITIVE MAMMARY CARCINOMA

CELL LINE: MCF7
MEDICAMENT: N-METHYL-CIS-4-HYDROXY-L-PROLINE + CIS-4-HYDROXY-L-PROLINE

LOW-MALIGNANCY ASTROCYTOMA
CELL LINE: HTZ-122
MEDICAMENT: CIS-4-HYDROXY-L-PROLINE

LOW-MALIGNANCY ASTROCYTOMA
CELL LINE: HTZ-122
MEDICAMENT: N-METHYL-CIS-4-HYDROXY-L-PROLINE + CIS-4-HYDROXY-L-PROLINE

HIGHLY MALIGNANT ASTROGLIOMA
CELL LINE: HTZ-17
MEDICAMENT: N-METHYL-CIS-4-HYDROXY-L-PROLINE

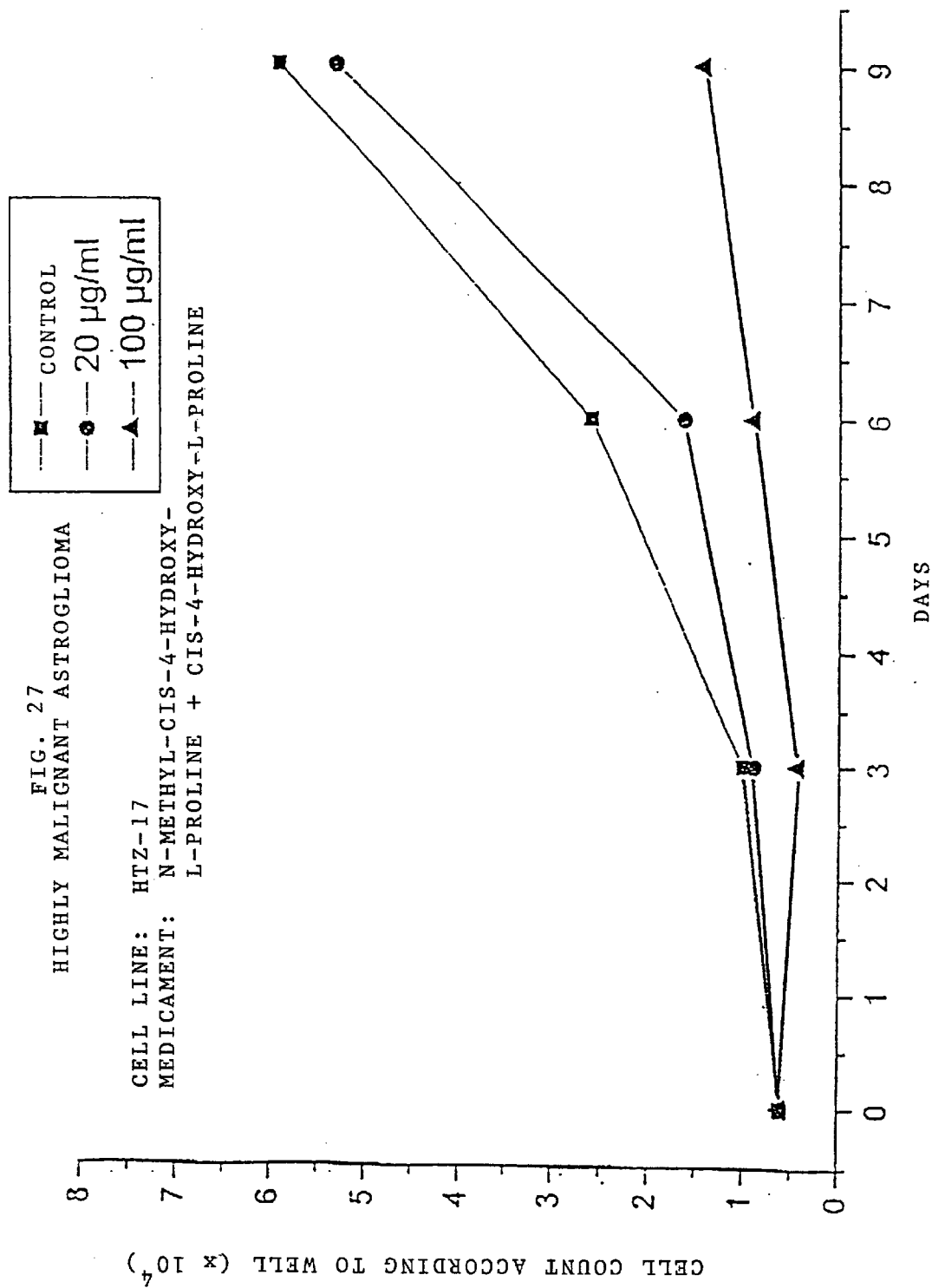

COMBINATION OF CIS-4-HYDROXY-L-PROLINE AND N-METHYL-CIS-4-HYDROXY-L-PROLINE FOR USE AS A THERAPEUTIC AGENT, IN PARTICULAR IN CANCER TREATMENT

INTRODUCTION

The invention relates to a combination of therapeutic agents, comprising as essential components:

(A) cis-4-hydroxy-L-proline and (B) N-methyl-cis-4-hydroxy-L-proline, or their pharmacologically compatible derivatives or precursors, for use as a therapeutic agent, particularly for therapy of cancer in humans. The invention further relates to drug formulations containing said combination, and use of same; and methods of treating cancer patients with said combination. Finally, the invention relates to the use of the individual components for therapy of hormone-sensitive prostate carcinoma.

TECHNICAL BACKGROUND

Ger. Pat. 3538619 discloses the use of cis-4-hydroxy-L-proline in the treatment of carcinomas and related tumors. Eur. AS B 0223850 discloses the use of N-methyl-cis-4-hydroxy-L-proline and N-methyl-trans-4-hydroxy-L-proline in treating astrocytoma cells. Said Eur AS refers to various other configurations, OH-positions, and alkylations, of the said derivatives of hydroxyproline and proline. W. Hoerrmann et al., 1987, Abstract No. 2:046, "Differential effects of cis-4-hydroxy-L-proline and methyl-cis-4-hydroxy-L-proline on tumour cells—evidence for redifferentiation and cell growth inhibition", in *Cancer detection and prevention*, 11, (1–2):66.

BRIEF DESCRIPTION OF DRAWINGS

FIG. 27 is a plot of HTZ-17 cell counts for various concentrations of the combination K.

THE INVENTION

Figure 1:
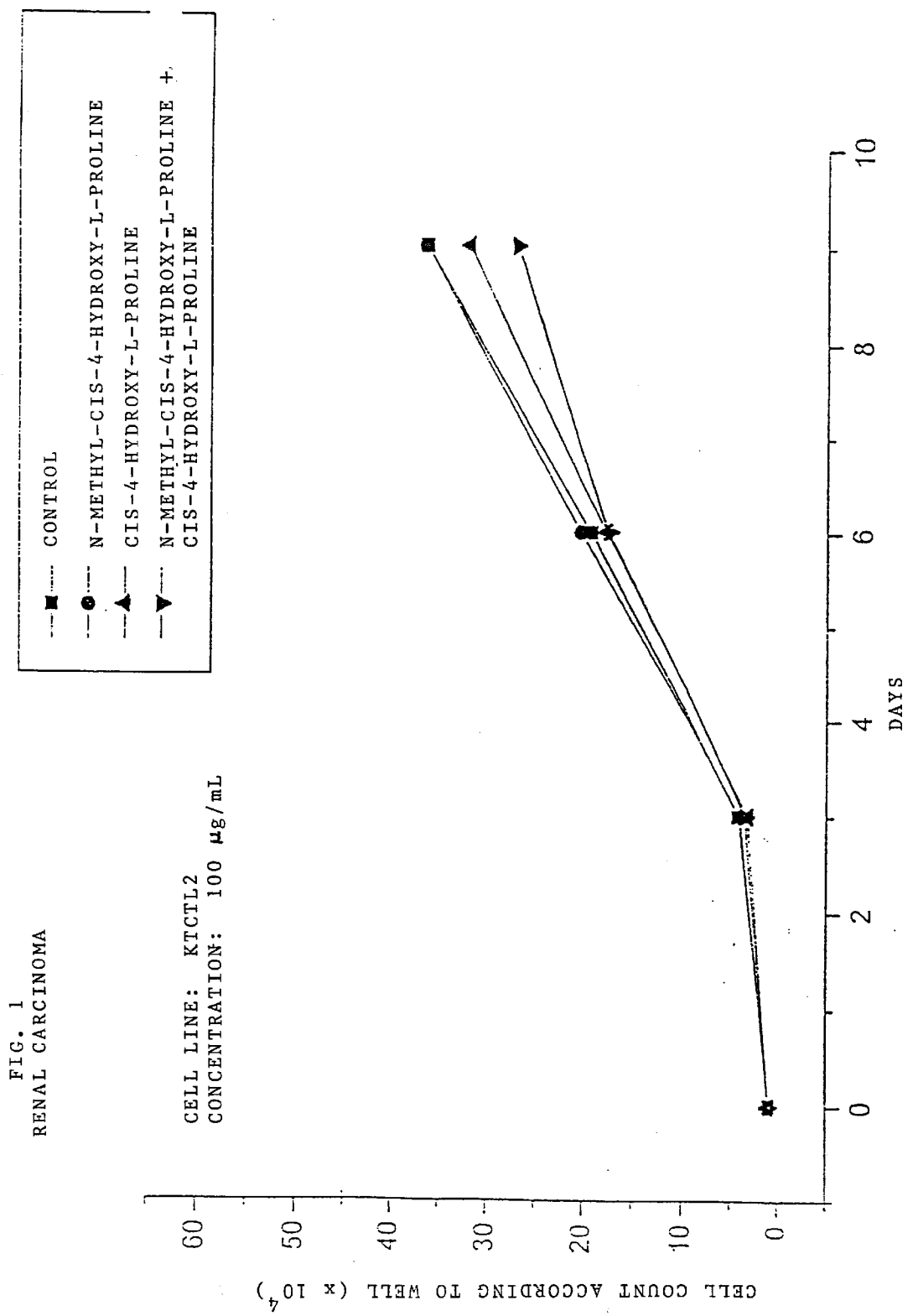
FIG. 1 is a graphic plot of KTCTL2 cell counts for component A, component B, and the combination K (A+B).
Figure 2:
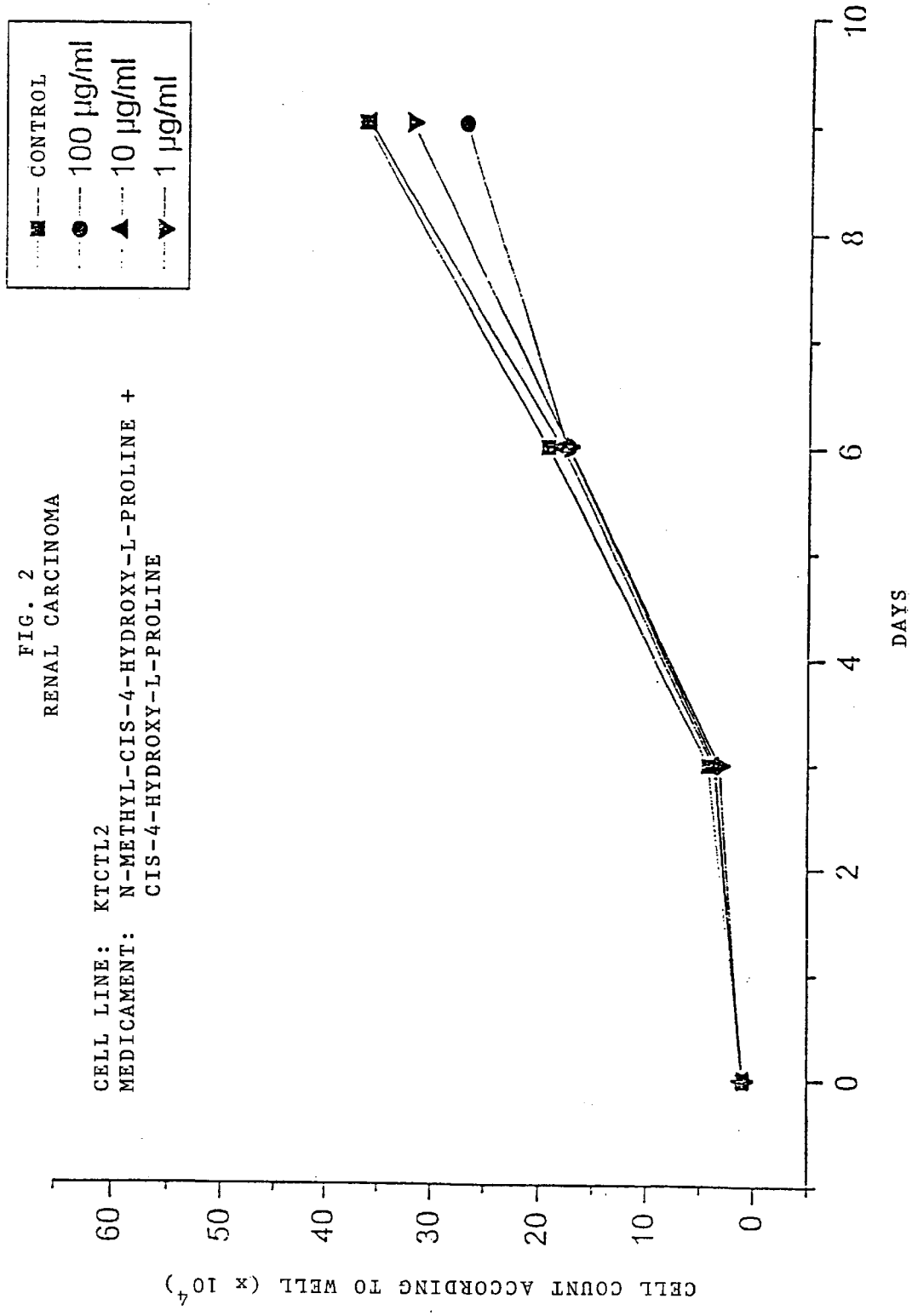
FIG. 2 is a plot of KTCTL2 cell counts for various concentrations of the combination K.
Figure 3:
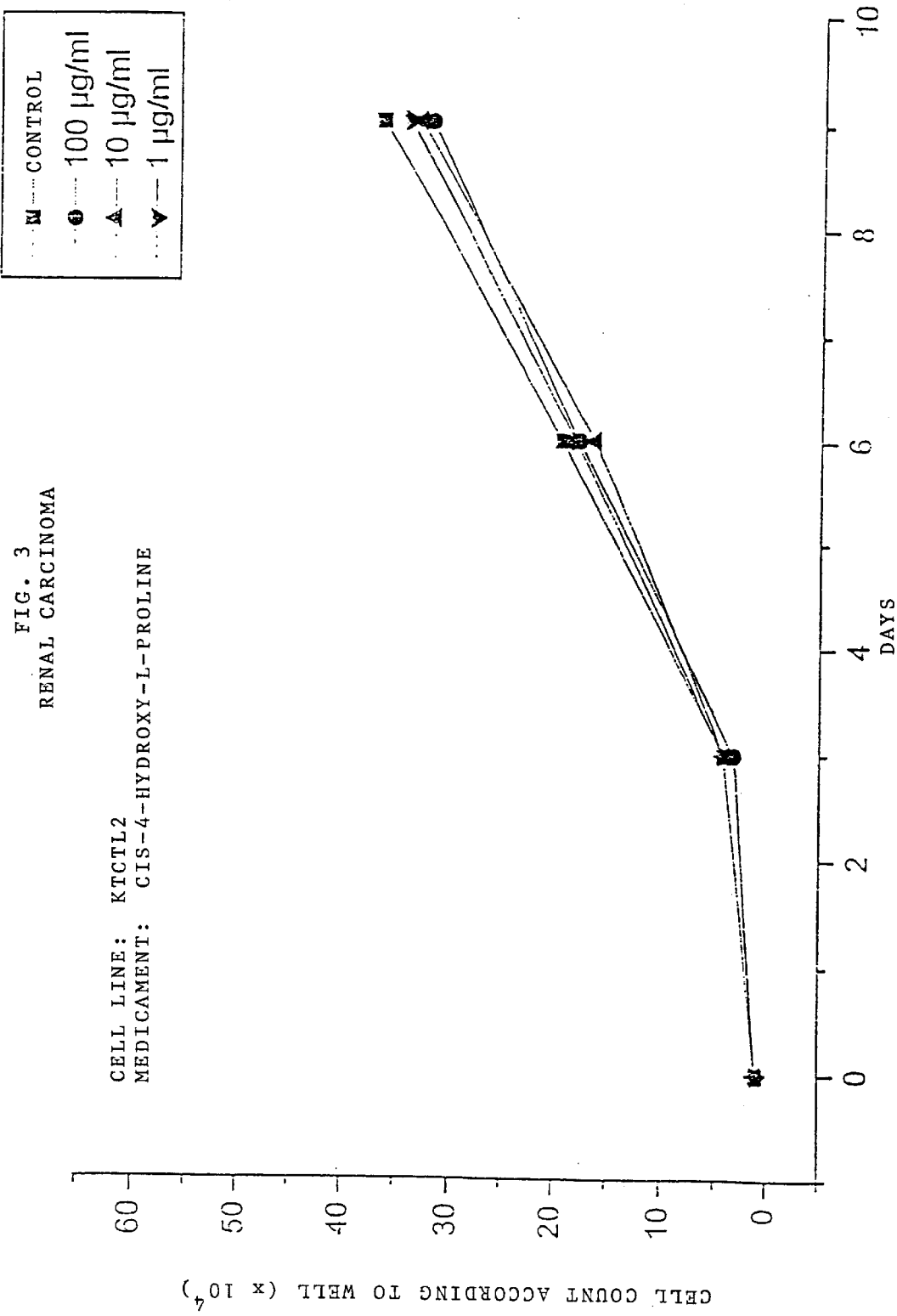
FIG. 3 is a plot of KTCTL2 cell counts for various concentrations of component A.
Figure 4:
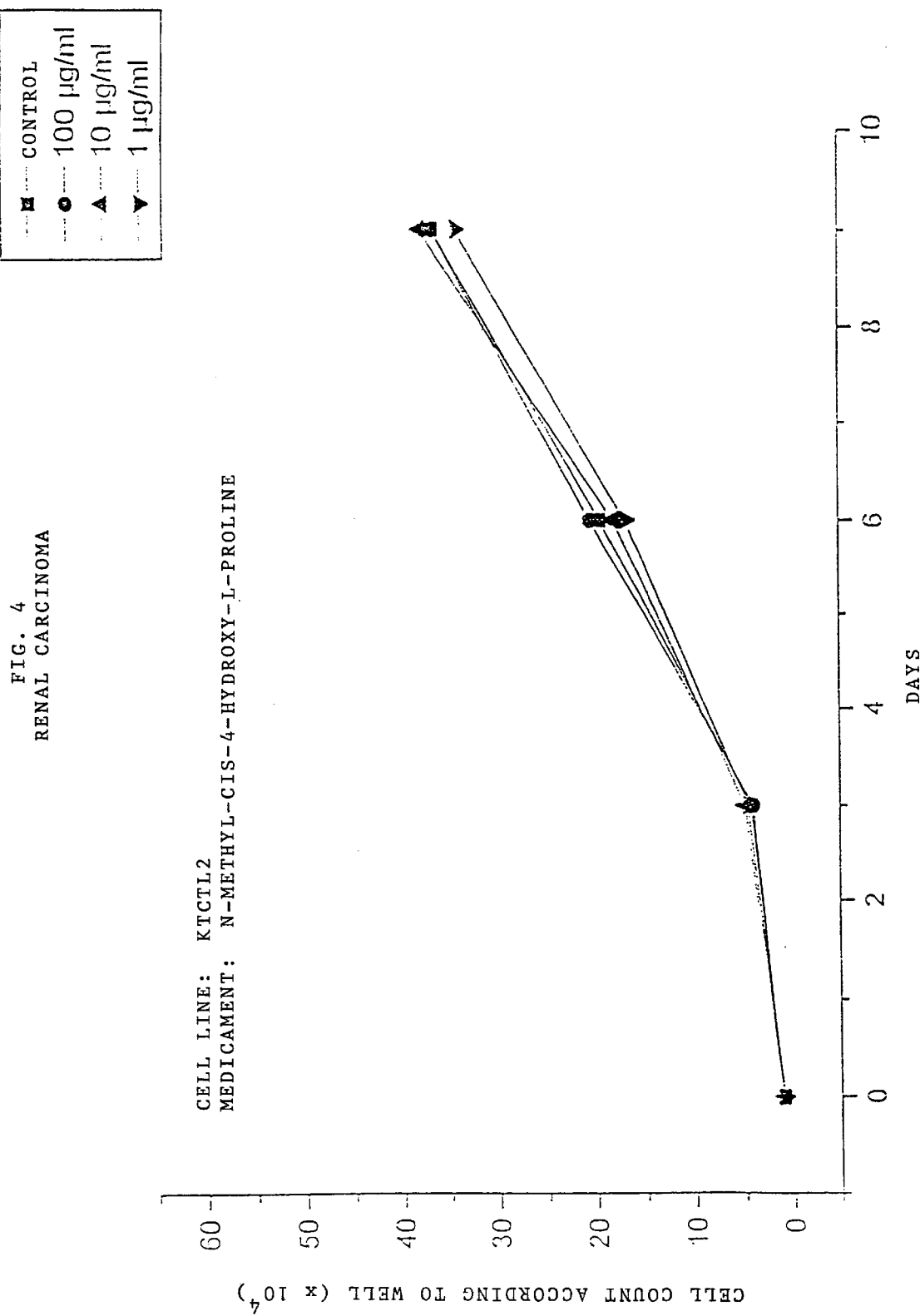
FIG. 4 is a plot of KTCTL2 cell counts for various concentrations of component B.

It was discovered, surprisingly, that the combination of components (A) and (B), is a valuable therapeutic agent, particularly in the therapy of tumors. The antitumor activity of the combination can be demonstrated particularly clearly in a cell culture of tumor cells, where it results in significant inhibition of cell proliferation. In tests of this nature, the tumor cells in a customary culture medium were treated with concentrations of the combination (molar ratio 1:1) in the range 1–100 μg/mL over a period of 6–10 da. At specific times the cell count was determined. Decrease in cell count or inhibition of cell proliferation is an important indicator of treatability of a tumor using the described combination.

As a rule, the inventive combination contains components (A) and (B) in a molar ratio which results in synergistic action, preferably a molar ratio in the range 10:1 to 1:10, particularly preferably a molar ratio of 1:1. Both components are nontoxic, with acute and subacute toxicities of greater than 10,000 mg/kg. Both components were found to be non-mutagenic in the Ames test.

Particular examples of treatable tumors the cells of which displayed inhibition of cell proliferation when treated with the inventive combination are: renal carcinomas, bladder carcinomas, prostate carcinomas, mammary carcinomas, brain tumors, and fibrosarcomas. Typical human tumor cell lines for testing the inventive combination may be obtained from various culture collections, e.g.: Deutsches Krebsforschungszentrum (German Cancer Research Center) (DKFZ), Heidelberg; American Type Culture Collection (ATCC), Rockville, Md., USA; and European Collection of Cell Cultures (ECACC), [at] Centre for Applied Microbiology and Research, Salisbury, Wiltshire, England.

The Examples serve to illustrate the invention, and should not be deemed to limit the scope thereof.

EXAMPLES

Tests of Inhibition of Cell Proliferation:

The following cell lines of human origin were used for tests of inhibition of cell proliferation using the inventive combination. The tests did not involve tumors implanted in hairless mice, because the chemical nature of components (A) and (B) is such that they could be metabolized by the host animals, with the attendant risk of false negative results.

1. Renal Carcinoma

KTCTL2—a renal carcinoma cell line from DKFZ Heidelberg. The cells have malignant characteristics, form tumors in hairless mice, and form colonies in Weichgar [(a certain agar medium)]. In cell cultures they grow with strong adhesion to the substrate.

SK Nep—another renal carcinoma cell line from DKFZ. SK Nep cells, like KTCTL2 cells, form tumors in hairless mice and form colonies in Weichgar. However, in cell cultures they have a more highly malignant phenotype, because they clearly exhibit spontaneous formation of small aggregates, and can grow above one another without contact inhibition, practically without dependence on adherence.

These two cell lines were selected because they have increasingly malignant characteristics in vitro.

2. Bladder Carcinoma Cells

RT-4: This cell line is derived from a highly differentiated papillary bladder carcinoma (Grade 1) in a man. This cell line grows in a strongly adhesion-dependent manner.

J82: This cell line is derived from a bladder carcinoma (Grade 3) with fully wild characteristics and low grade differentiation.

3. Prostate Carcinoma Cells

PC-3: A cell line from a progressive hormone-resistant prostate carcinoma. It is highly tumorous in hairless mice, and forms colonies in Weichgar.

LNCaP: A cell line from a lymph node metastasis of a hormone-sensitive medium-grade differentiated prostate carcinoma.

4. Mammary Carcinoma Cells

The cell line MCF 7 was used. It is estrogen-sensitive.

5. Fibrosarcoma Cells

The cell line HT 1080 was used.

6. Brain Tumor Cells

The cell lines HTZ-122 and HTZ-17 were used. HTZ-122 is an astrocytoma of low malignancy (WHO Grade I). HTZ-17 is an astrocytic tumor of high malignancy (glioblastoma multiforme, WHO Grade IV).

The following treatment tests were carried out with the described cell lines:

Test type 1: The component (A), was used individually, in various concentrations.

Test type 2: The component (B), was used individually, in various concentrations.

Test type 3: The combination (K) of components (A) and (B), in a molar ratio 1:1, was used in various concentrations.

The results of all of these tests are indicated in the accompanying graphic plots, which show the cell counts, test duration (days), and concentrations used.

The following is a discussion of the accompanying plots:

With the renal carcinoma cells KTCTL2, the individual components (A) and (B) had no effects. In contrast, the combination (K) of the two components led to significant and dose-dependent growth inhibition of c. 25% (see FIGS. 1–4). Thus the combination displays a true cooperative (synergistic) inhibition of cell proliferation in KTCTL2 cells, which inhibition cannot be attained by treatment with either of the individual substances alone.

SK Nep, which has a particularly malignant phenotype, was not affected by (K) or (A) or (B).

Figure 5:
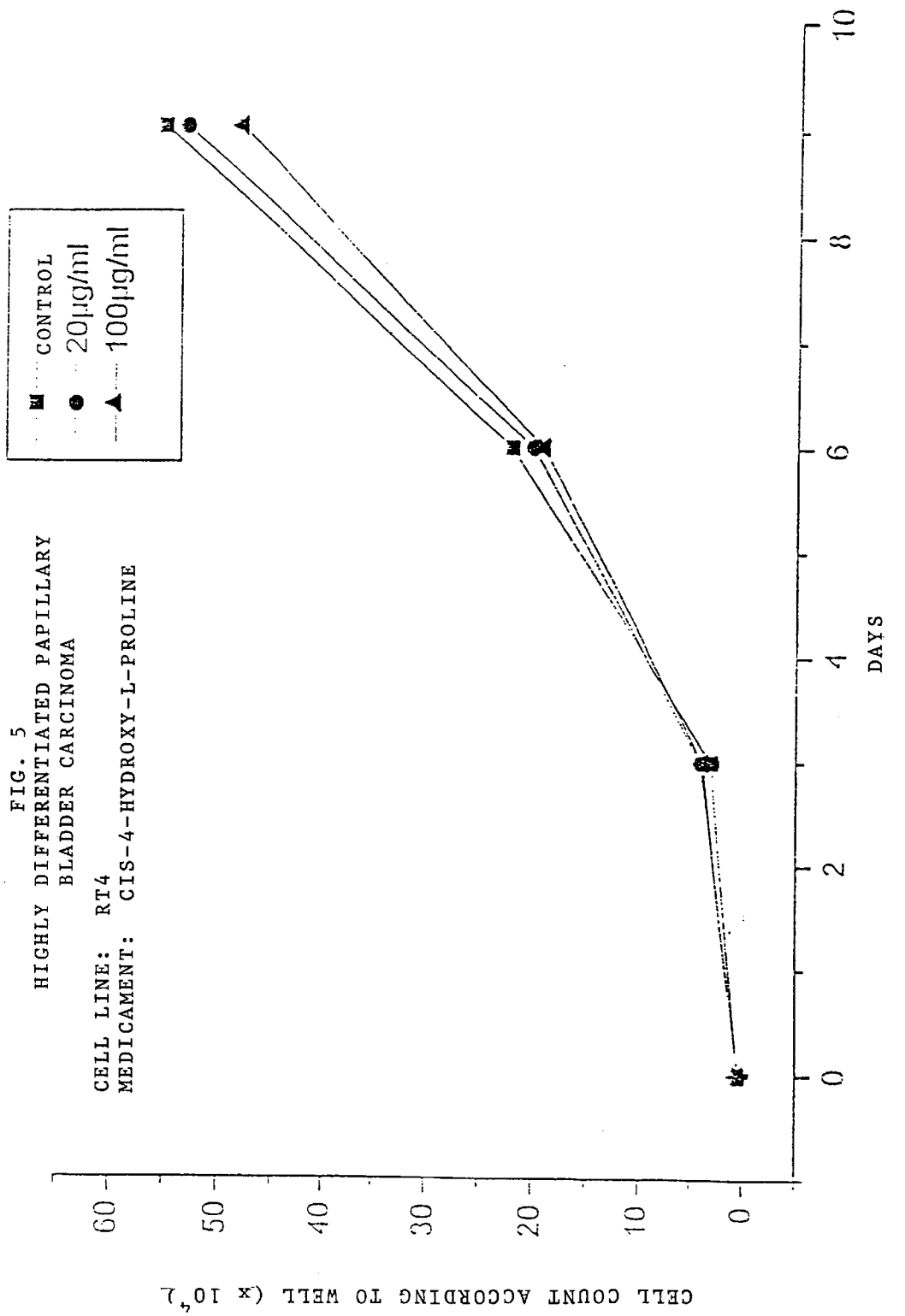
FIG. 5 is a plot of RT4 cell counts for various concentrations of component A.
Figure 6:
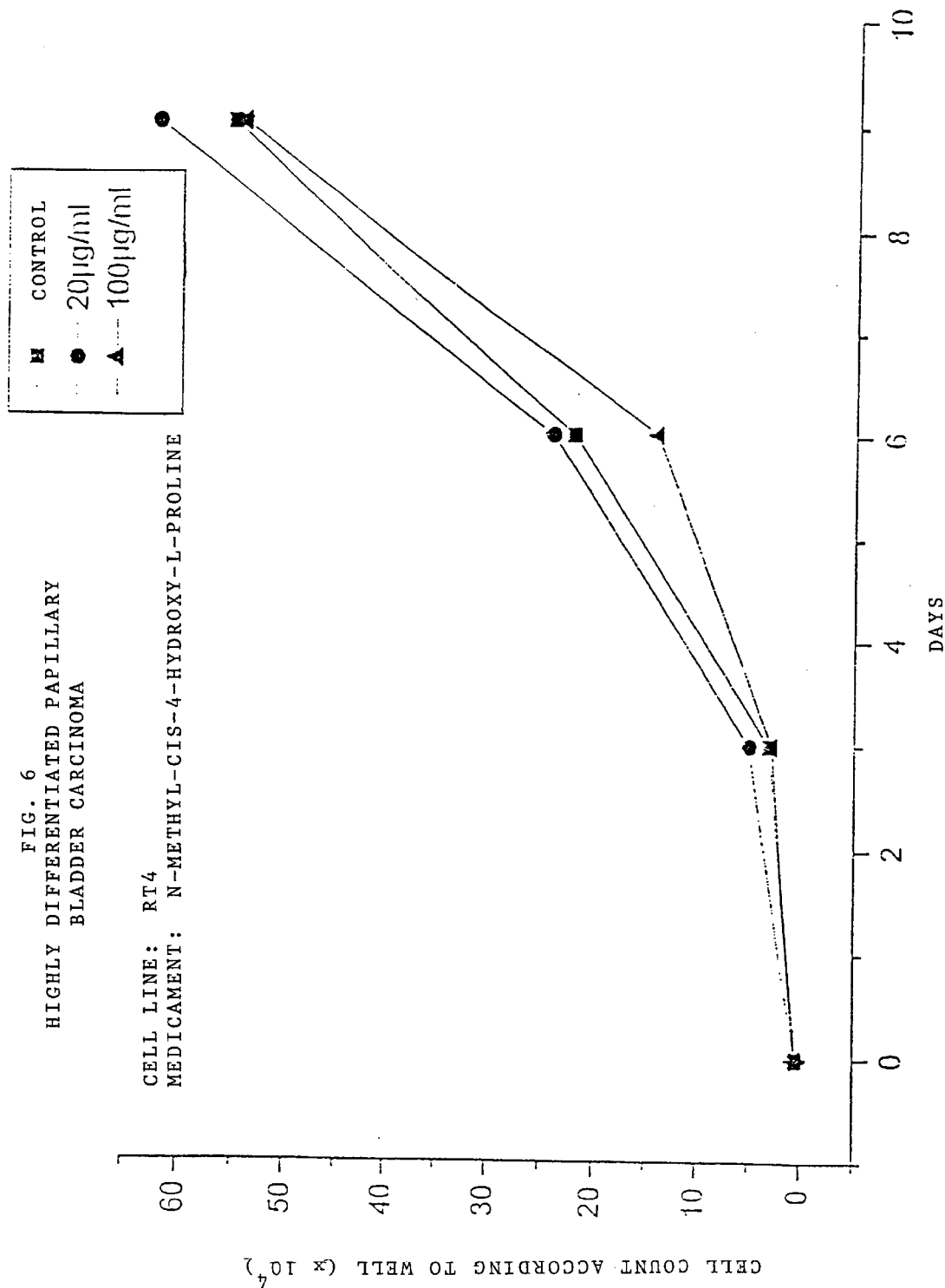
FIG. 6 is a plot of RT4 cell counts for various concentrations of component B.
Figure 7:
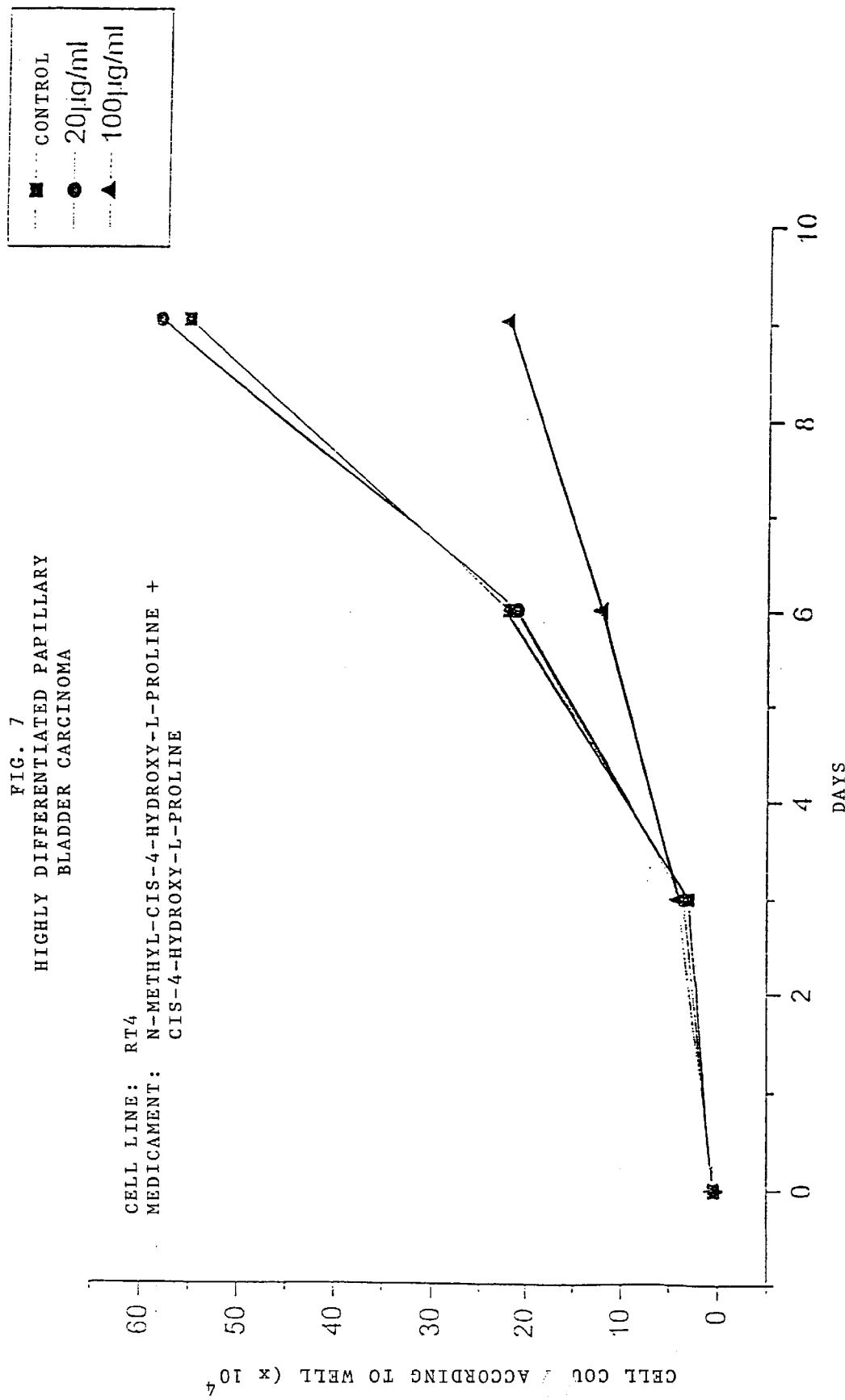
FIG. 7 is a plot of RT4 cell counts for various concentrations of the combination K.

The combination (K) had an impressively strong synergistic effect on cell line RT-4 from a papillary bladder carcinoma in a man. The individual substances had practically no effect, even at 100 µg/mL; in contrast, the combination (K) substantially inhibited cell proliferation (see FIGS. 5–7).

Figure 8:
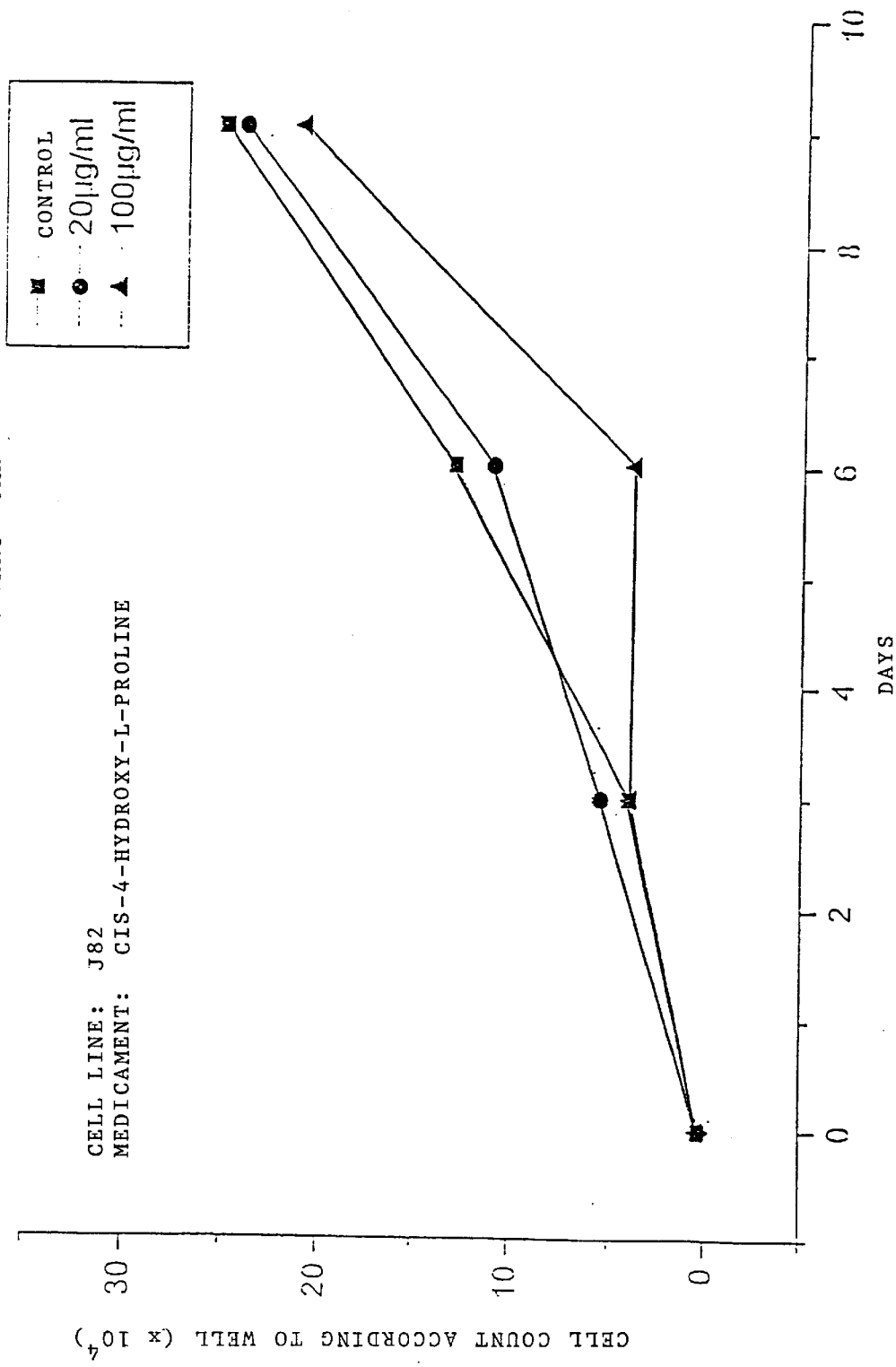
FIG. 8 is a plot of J82 cell counts for various concentrations of component A.
Figure 9:
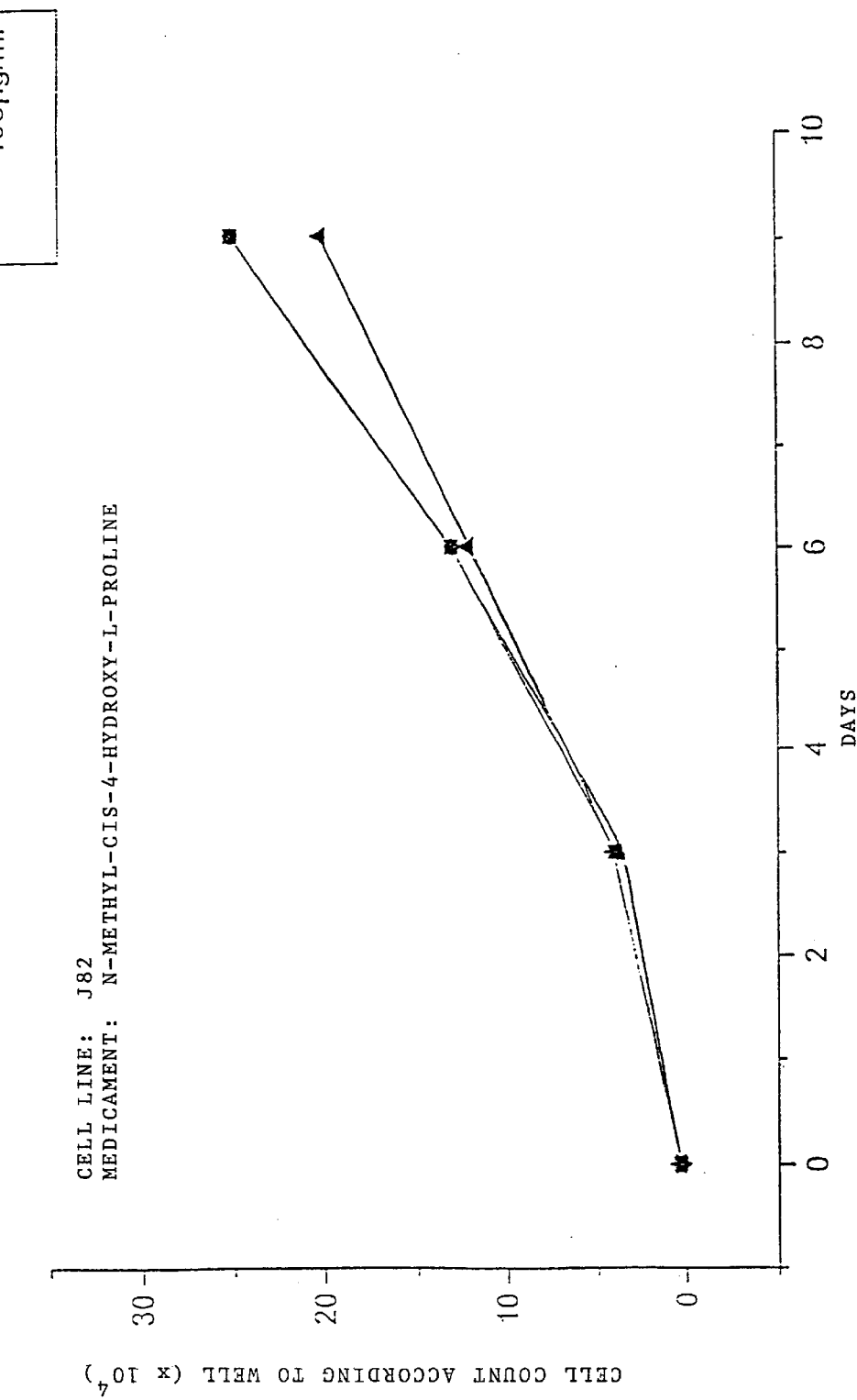
FIG. 9 is a plot of J82 cell counts for various concentrations of component B.
Figure 10:
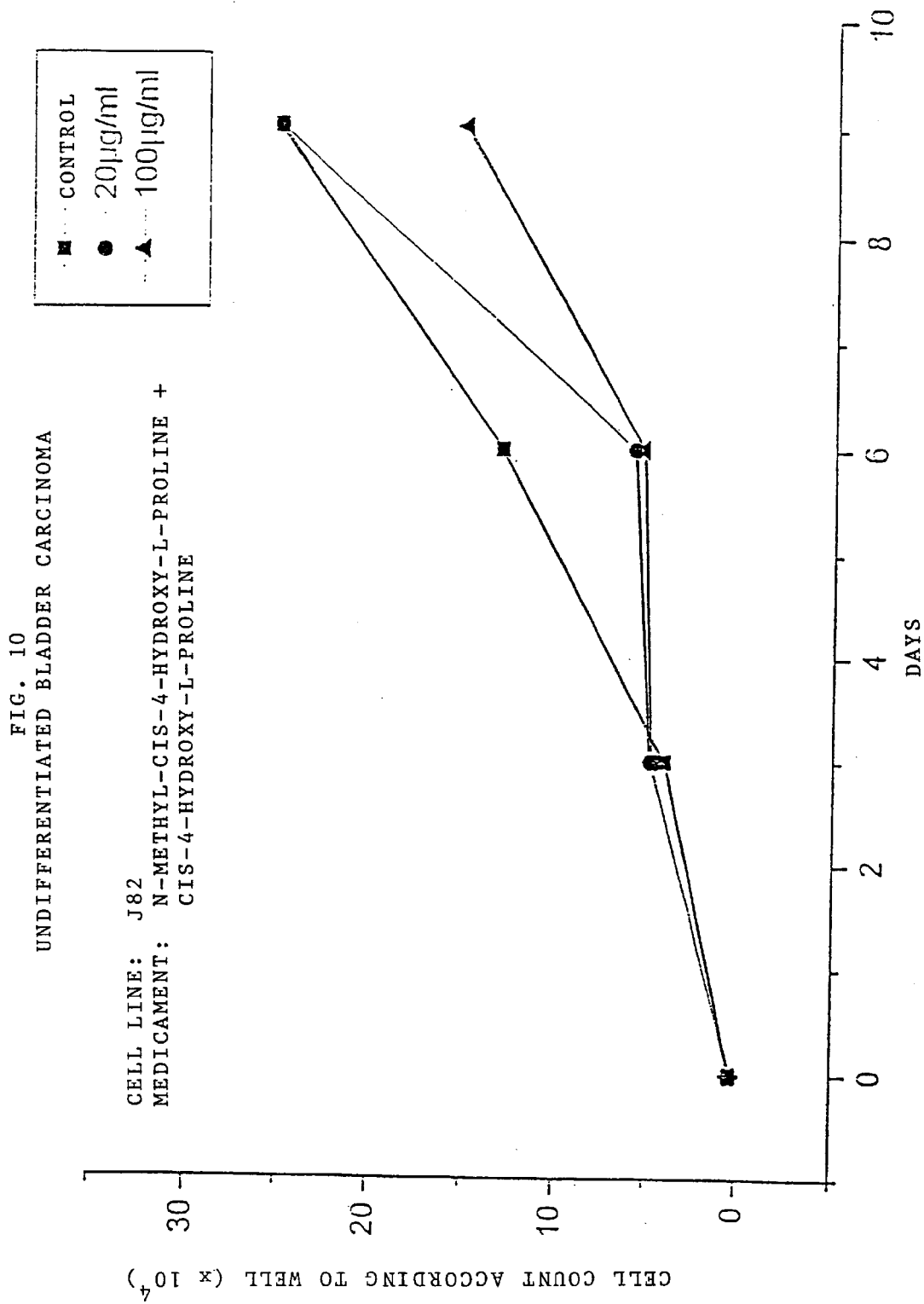
FIG. 10 is a plot of J82 cell counts for various concentrations of the combination K.

The low-differentiated bladder carcinoma J 82 with fully wild characteristics was not affected by the individual components (A) or (B); the combination (K) had a moderate effect (see FIGS. 8–10).

Figure 11:
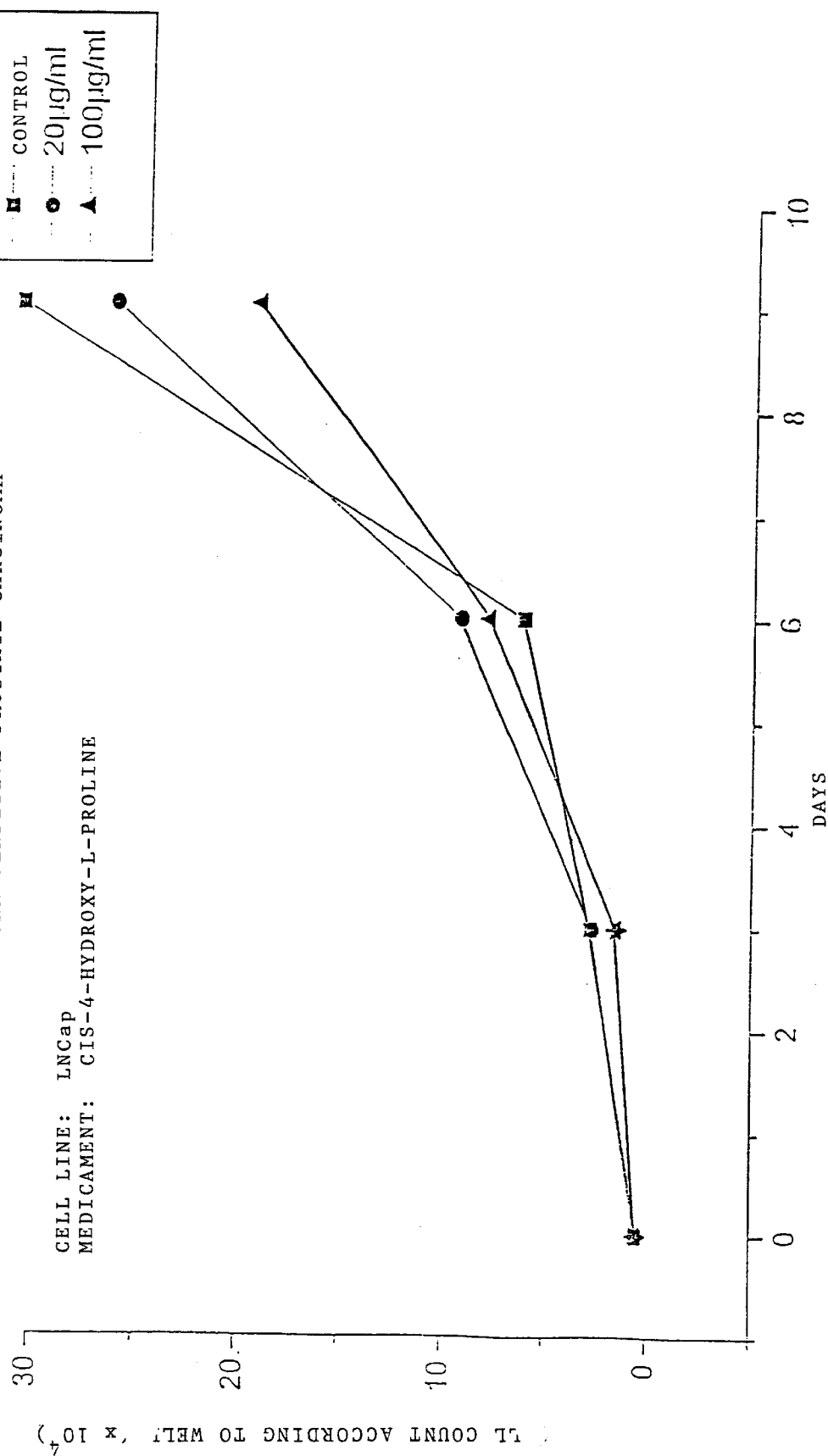
FIG. 11 is a plot of LNCap cell counts for various concentrations of component A.
Figure 12:
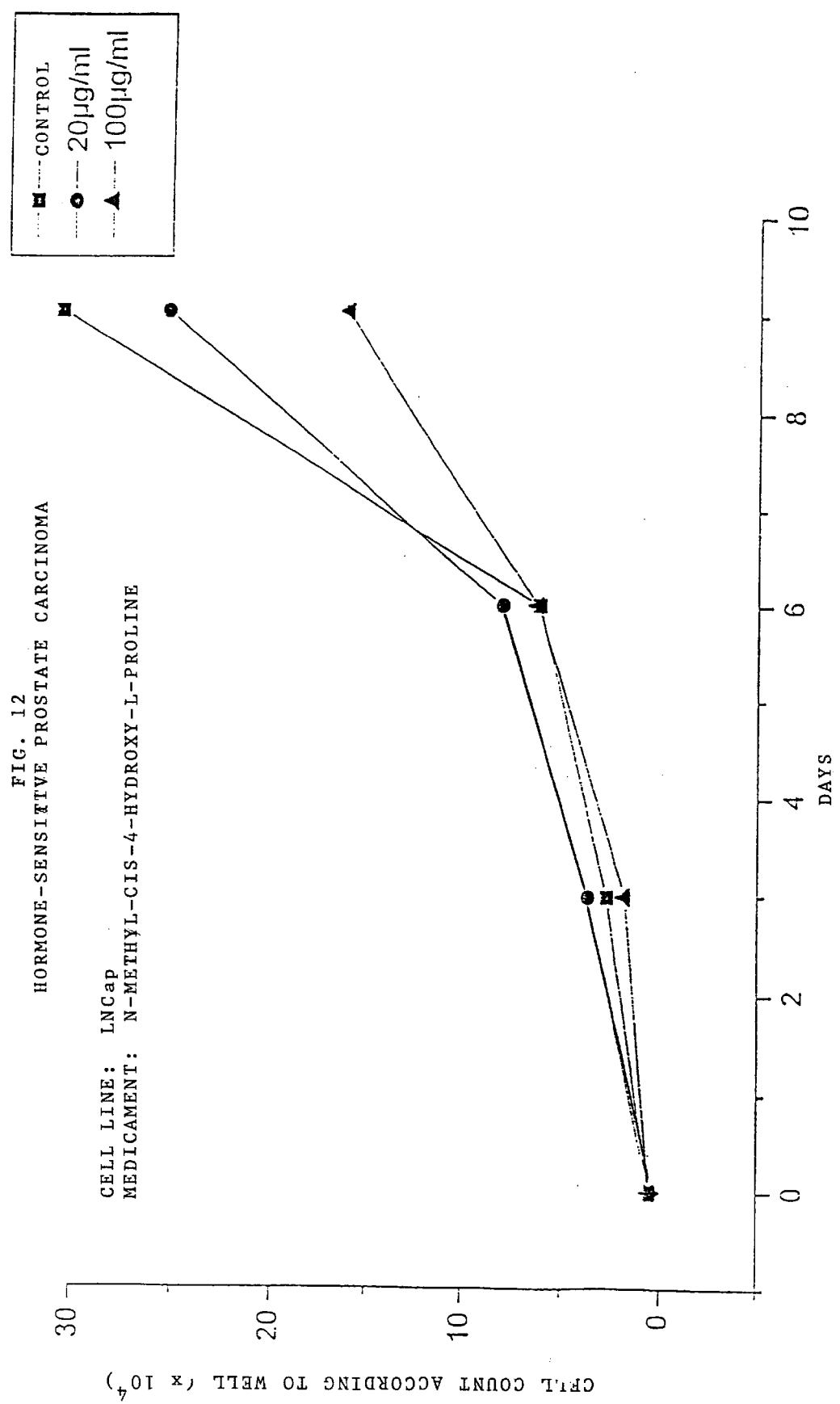
FIG. 12 is a plot of LNCap cell counts for various concentrations of component B.
Figure 13:
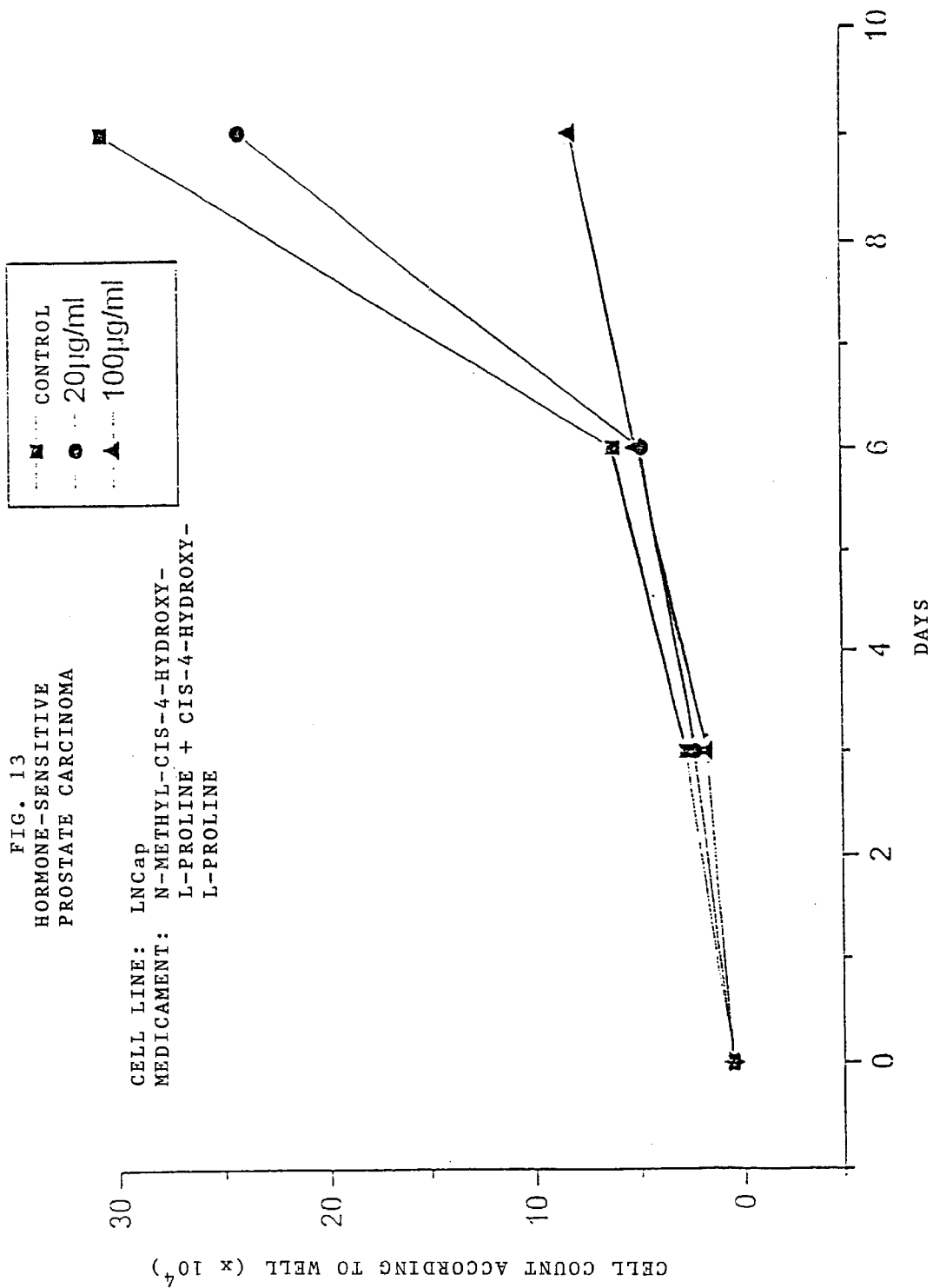
FIG. 13 is a plot of LNCap cell counts for various concentrations of the combination K.

With the hormone-sensitive prostate carcinoma cell line LNCap, the individual components (A) and (B) were found to have significant inhibiting effects; the combination (K) had even stronger inhibiting effects (see FIGS. 11–13).

Figure 14:
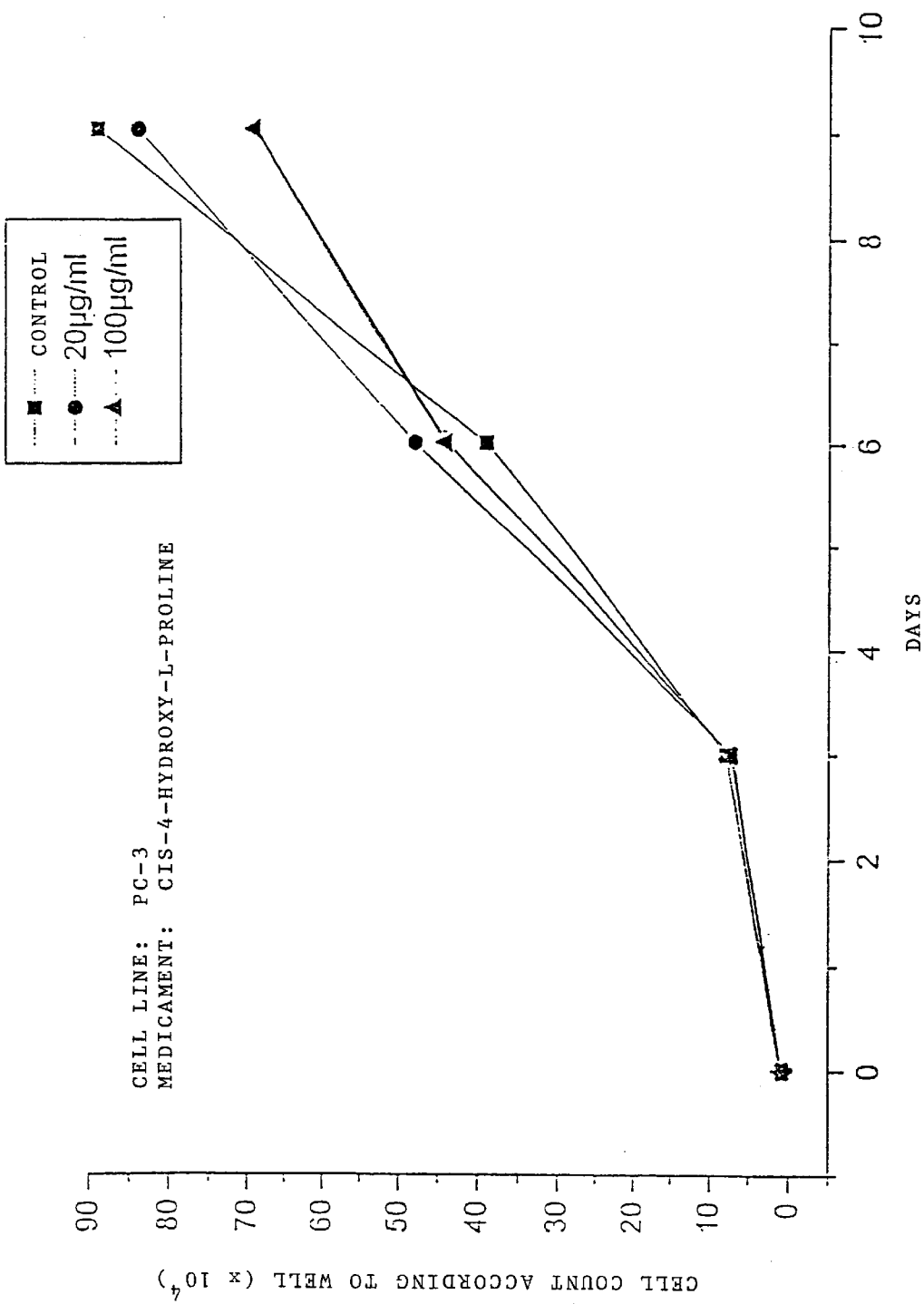
FIG. 14 is a plot of PC-3 cell counts for various concentrations of component A.
Figure 15:
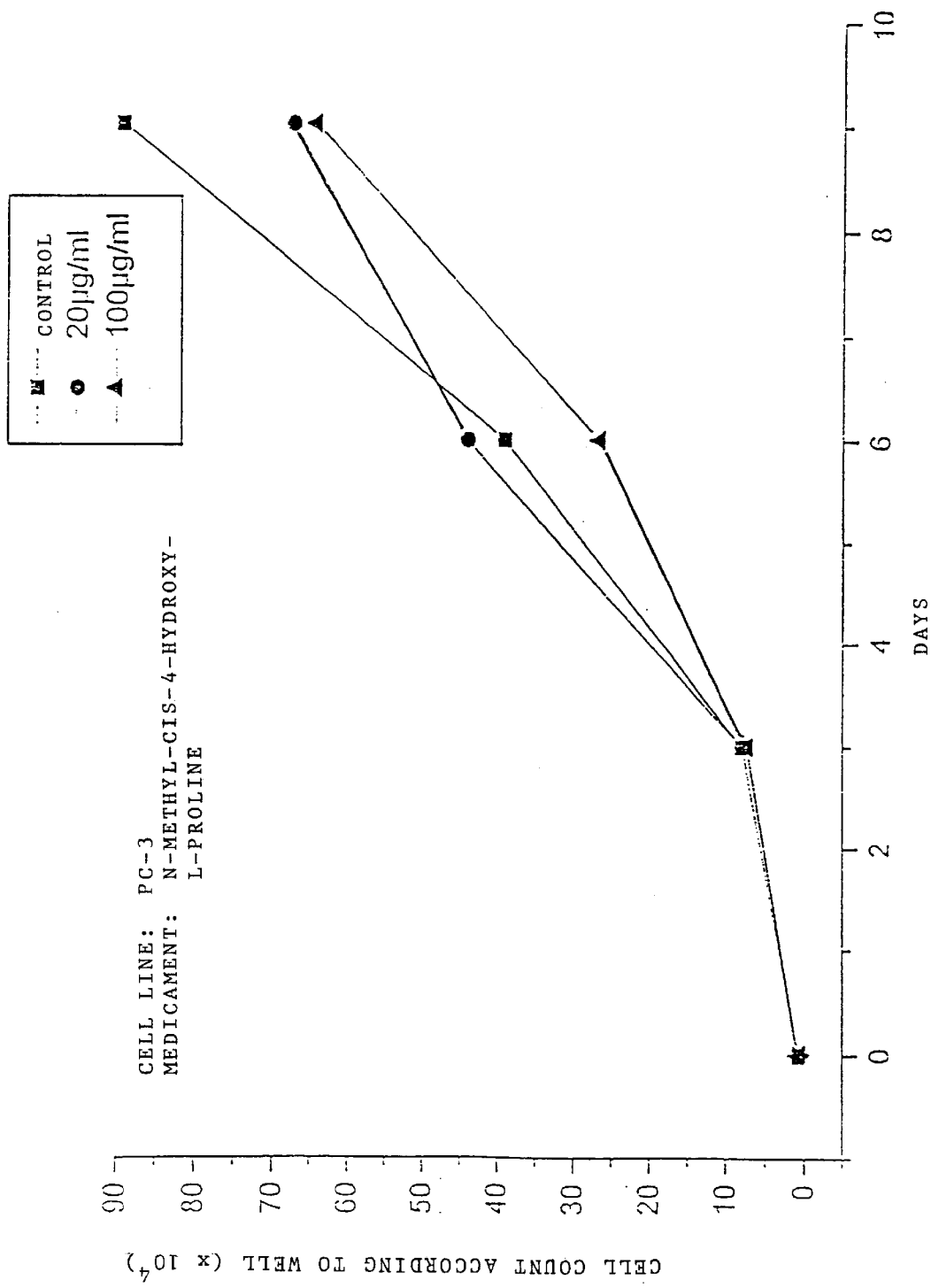
FIG. 15 is a plot of PC-3 cell counts for various concentrations of component B.
Figure 16:
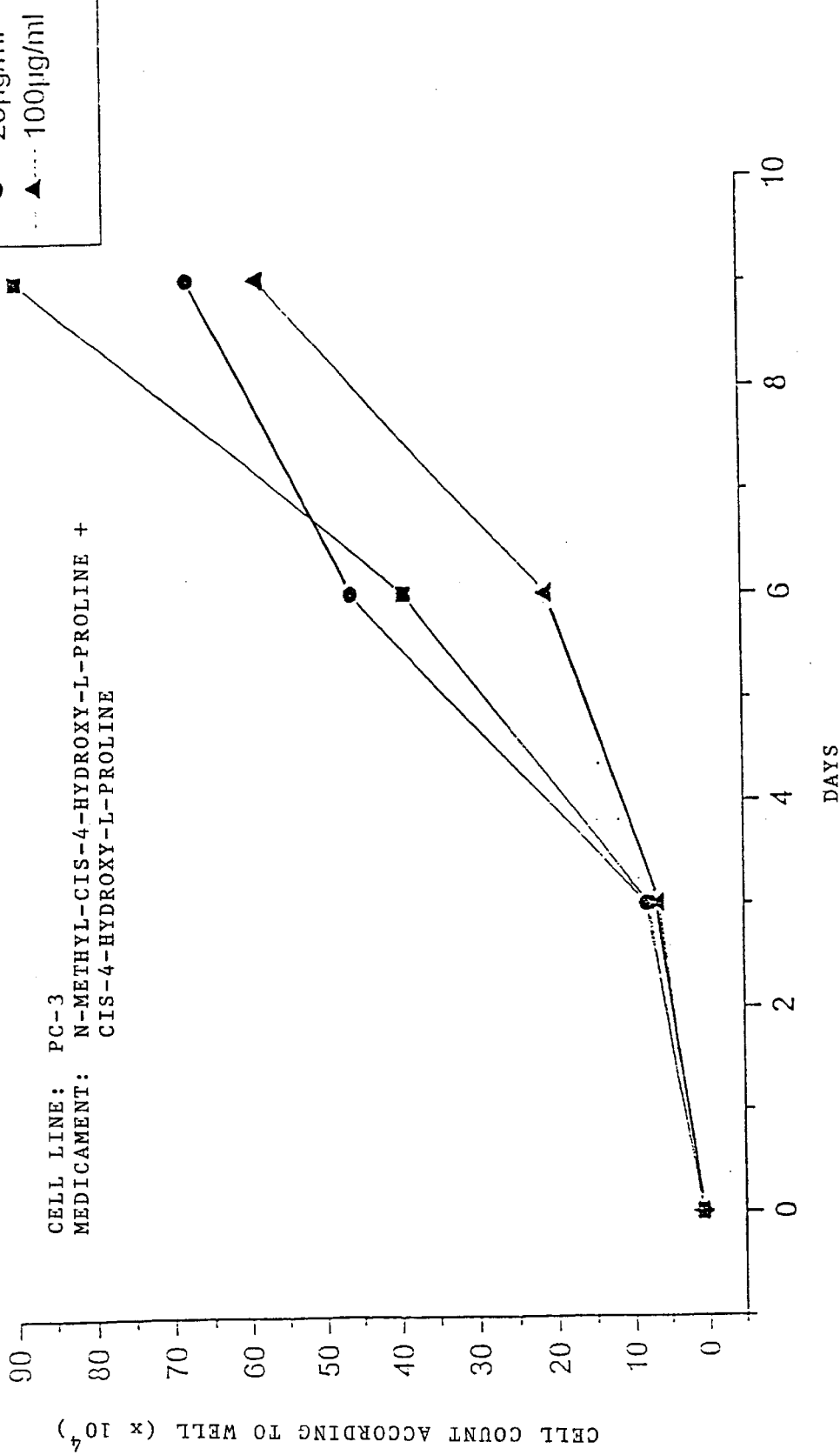
FIG. 16 is a plot of PC-3 cell counts for various concentrations of the combination K.

With the hormone-resistant prostate carcinoma cell line PC 3, the individual components (A) and (B) and the combination (K) all had weak effects (see FIGS. 14–16).

The differing effects with these two prostate carcinoma cell lines demonstrate the high specificity of the subject compounds.

Figure 17:
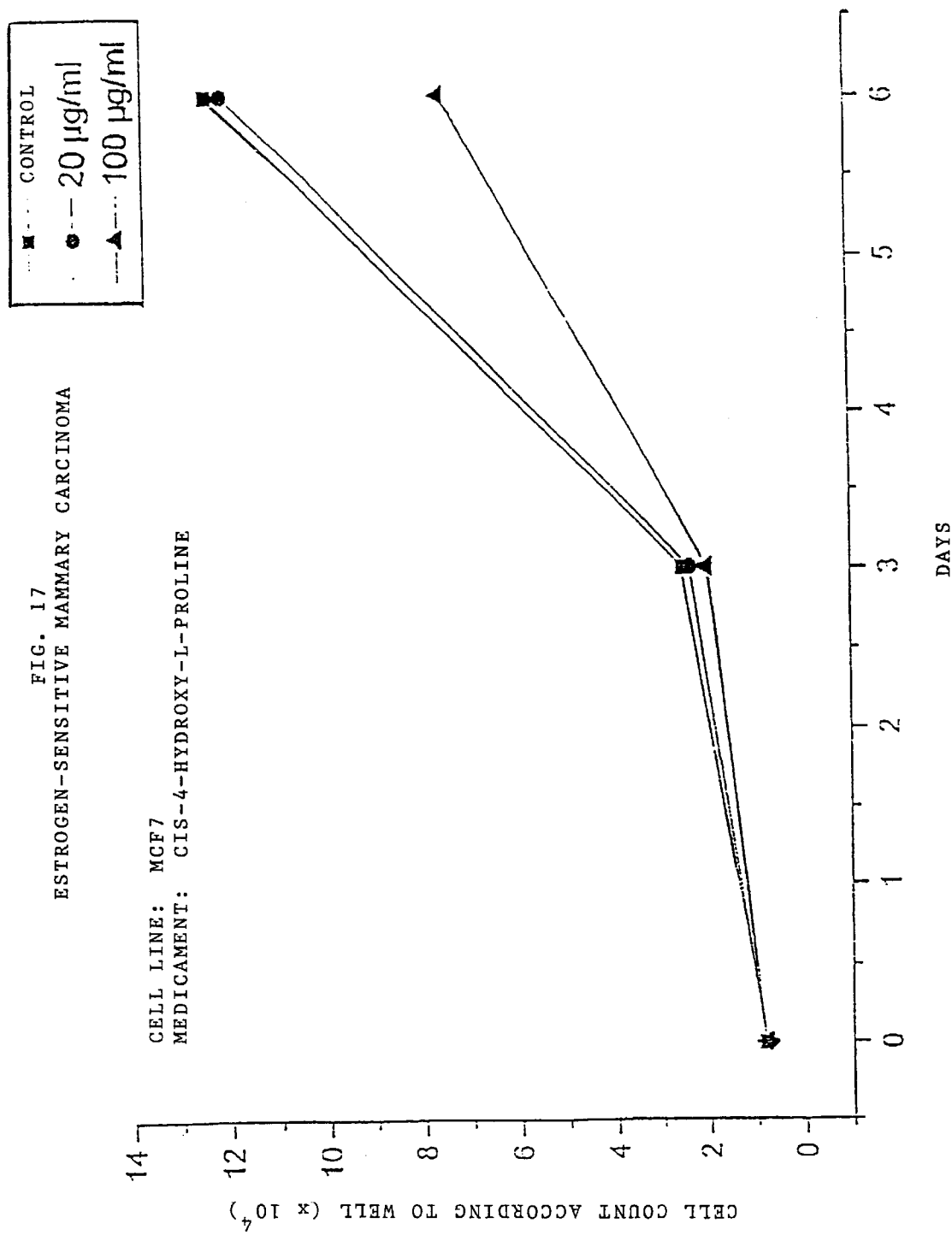
FIG. 17 is a plot of MCF7 cell counts for various concentrations of component A.
Figure 18:
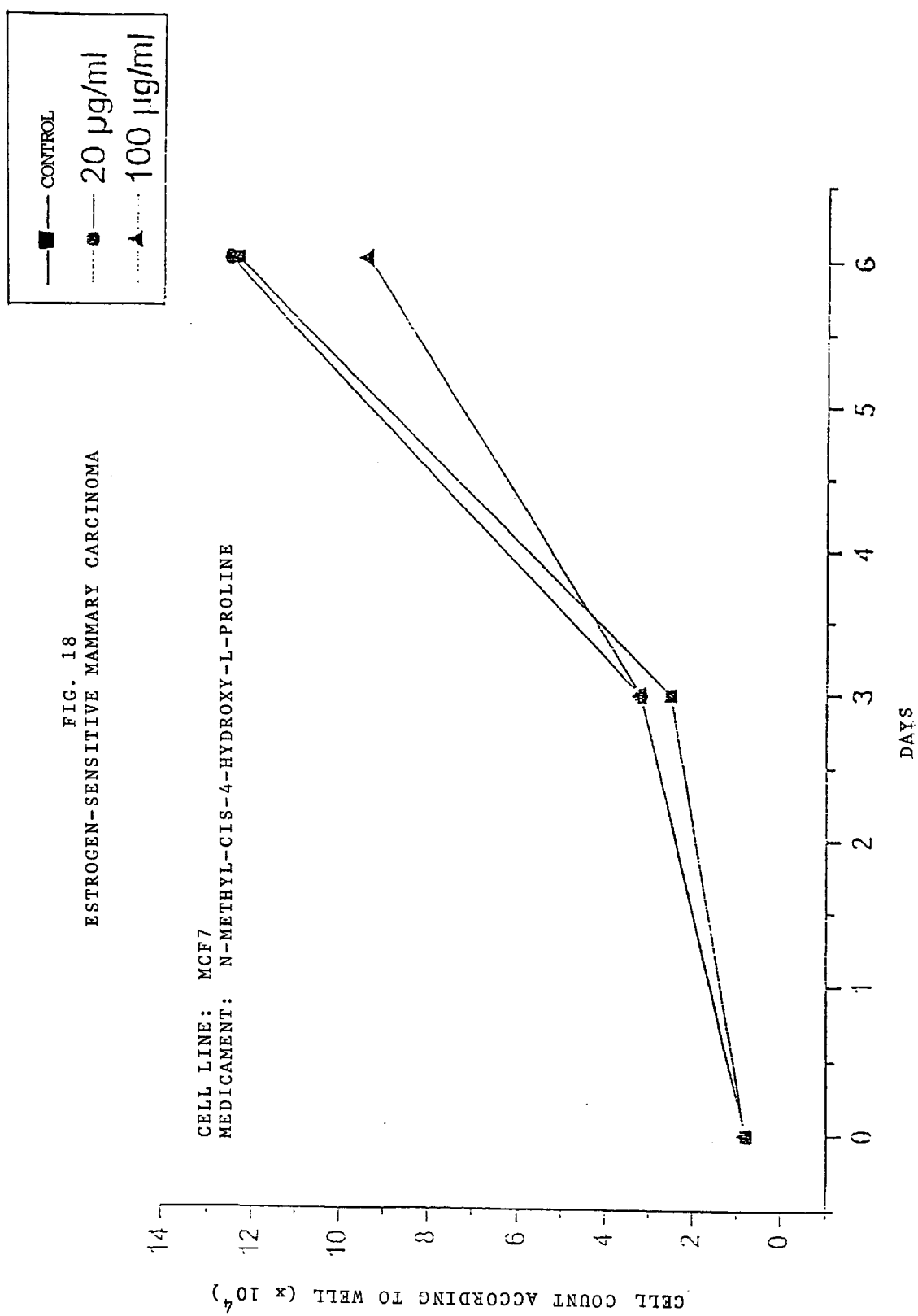
FIG. 18 is a plot of MCF7 cell counts for various concentrations of component B.
Figure 19:
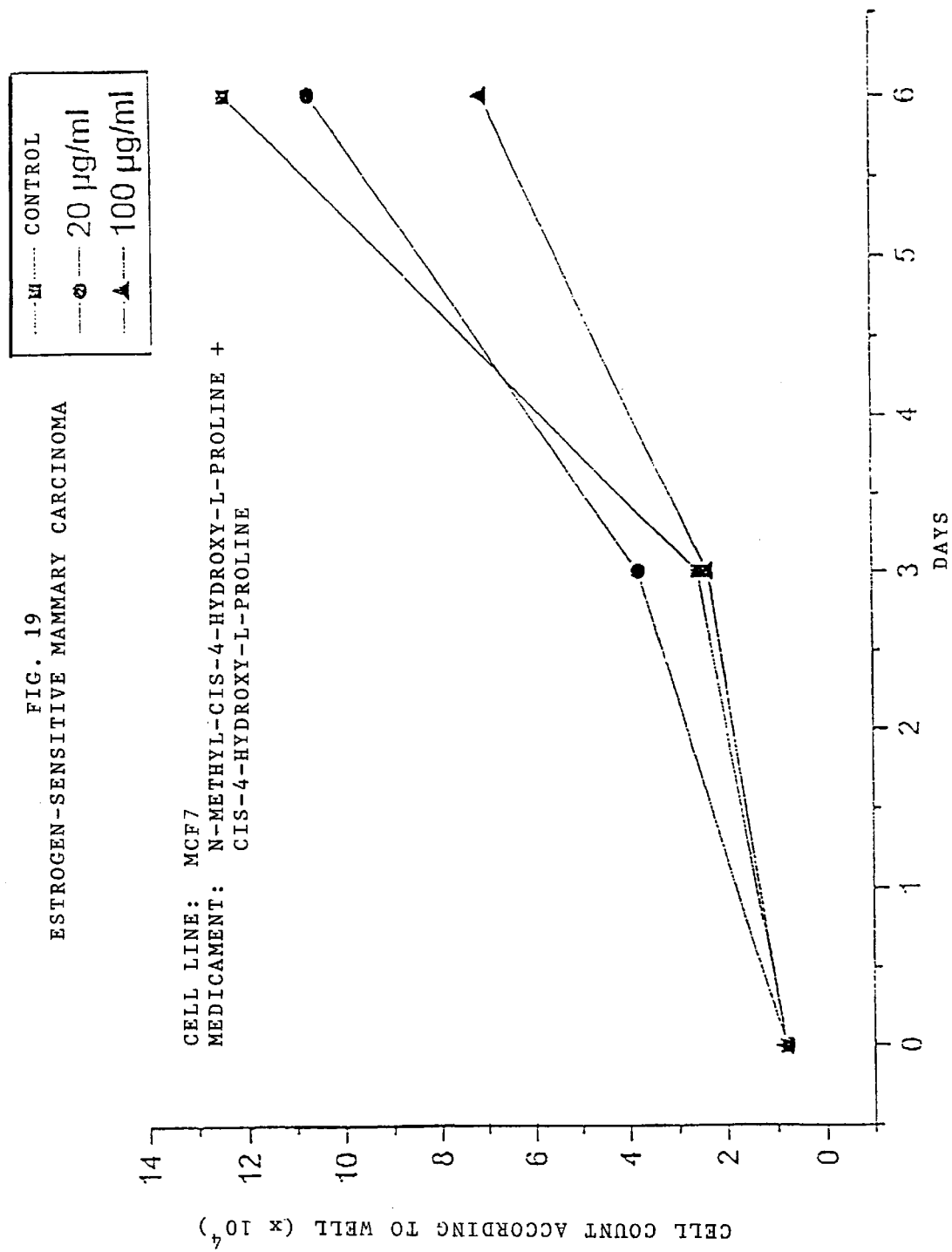
FIG. 19 is a plot of MCF7 cell counts for various concentrations of the combination K.

With the estrogen-sensitive mammary carcinoma cell line MCF 7, the individual components (A) and (B) and the combination (K) displayed inhibitions of up to 50%, but only for the combination could it be shown that the effect was dose-dependent See FIGS. 17–19.

Figure 20:
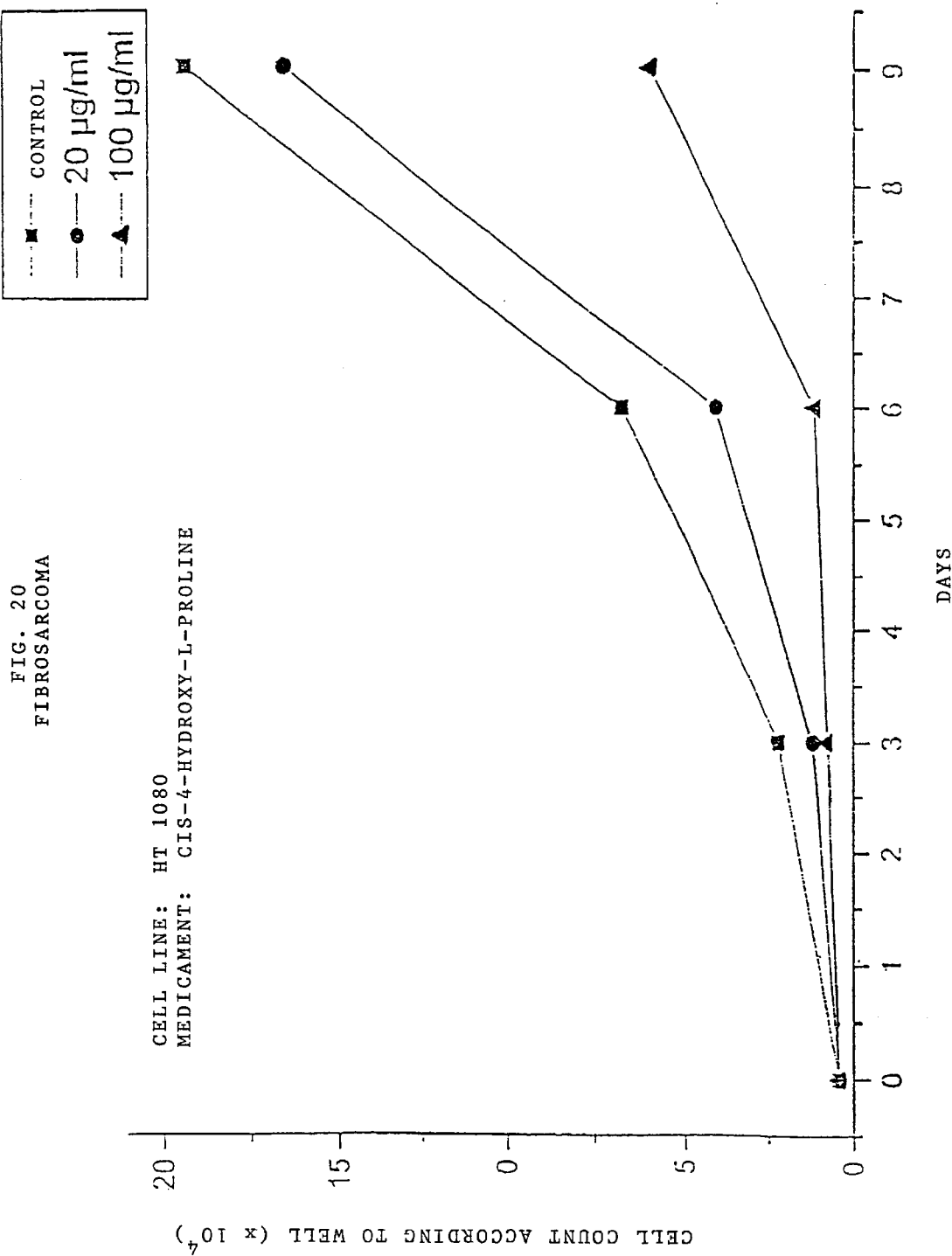
FIG. 20 is a plot of HT 1080 cell counts for various concentrations of component A.
Figure 21:
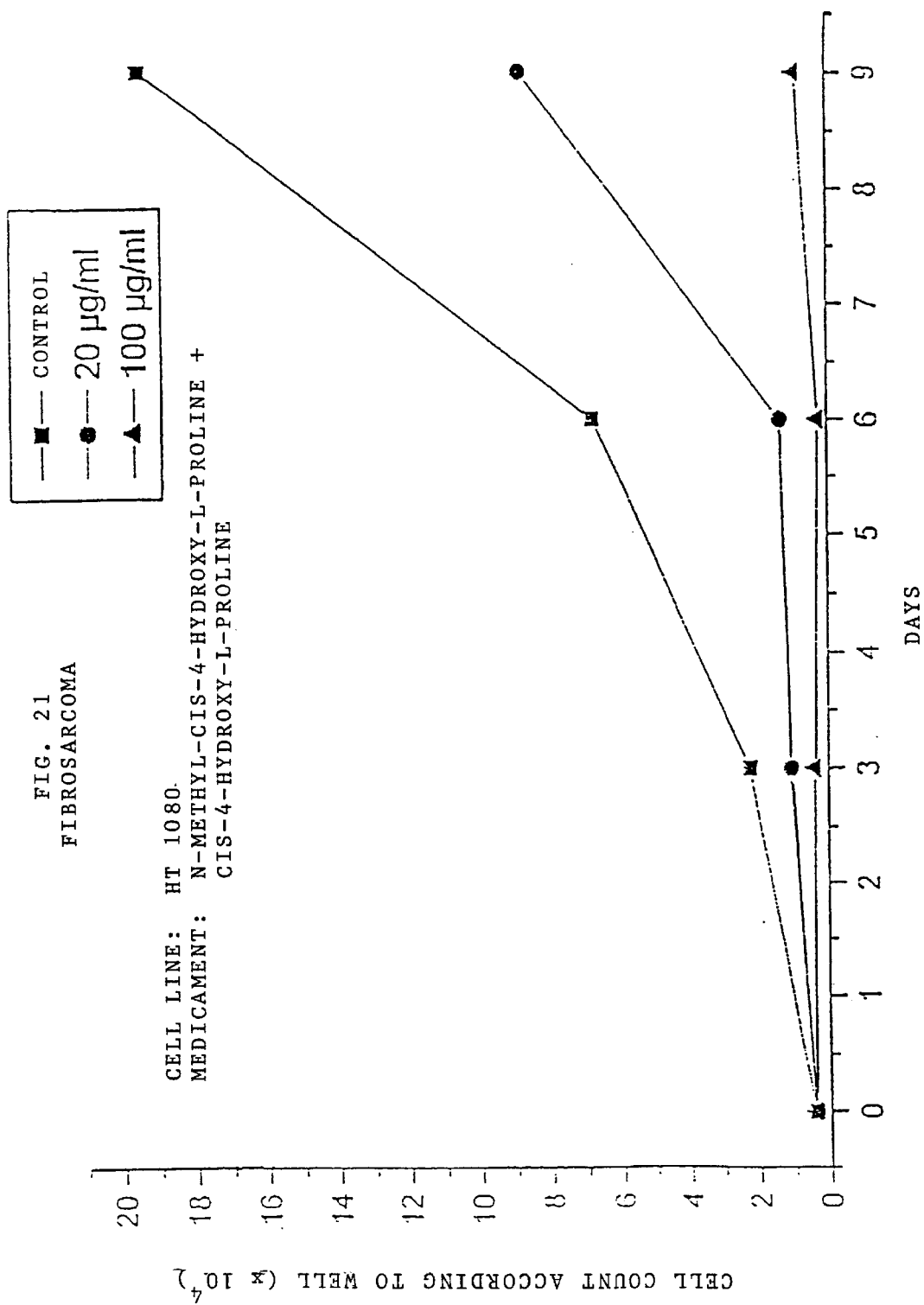
FIG. 21 is a plot of HT 1080 cell counts for various concentrations of the combination K.

With the fibrosarcoma cell line HT 1080, the individual component (A) displayed a strong effect, the individual component (B) provided a curve which could not be clearly evaluated, and the combination (K) showed outstanding activity, with inhibition of cell proliferation which was dose-dependent and amounted to more than 90% See FIGS. 20–21.

Figure 22:
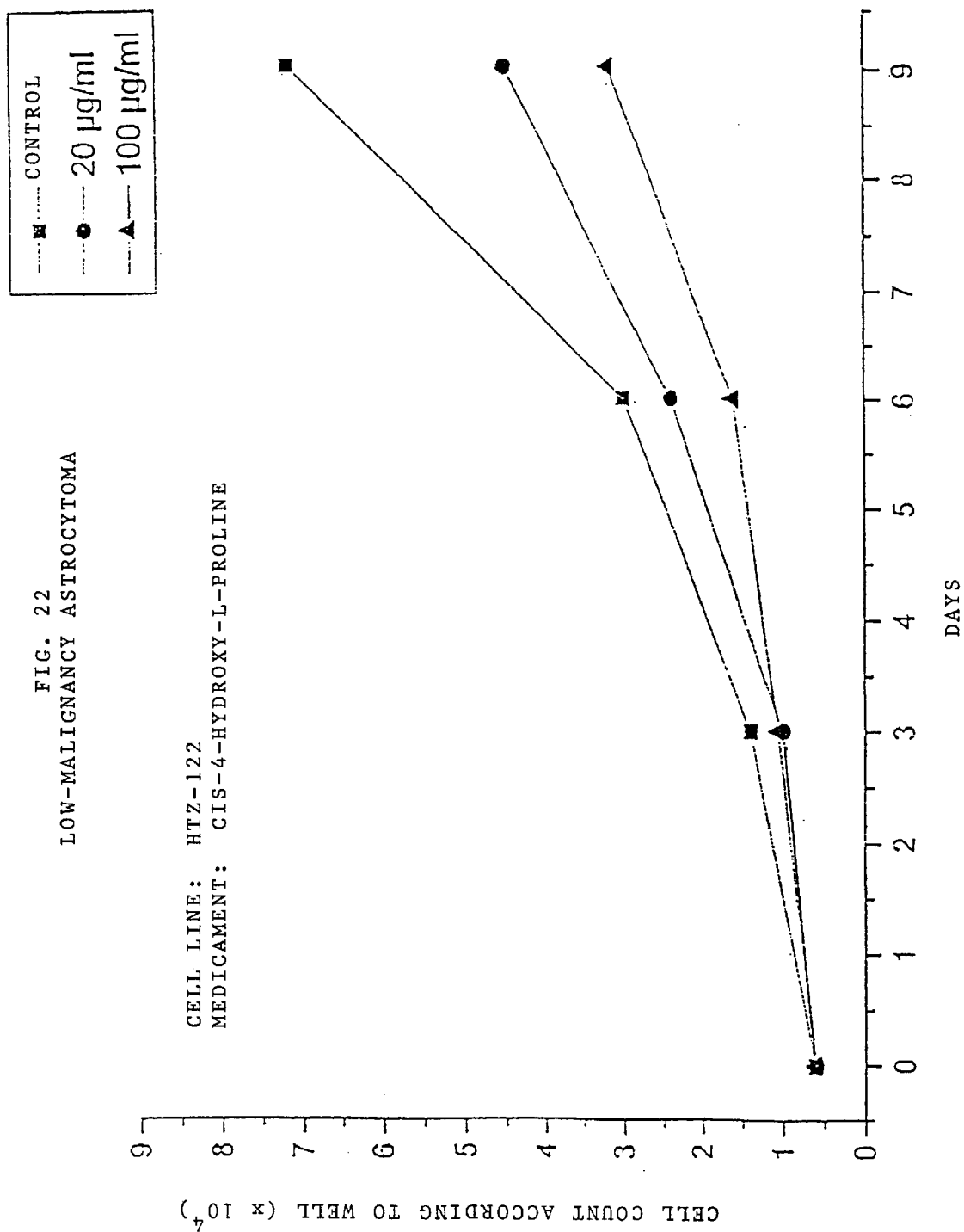
FIG. 22 is a plot of HTZ-122 cell counts for various concentrations of component A.
Figure 23:
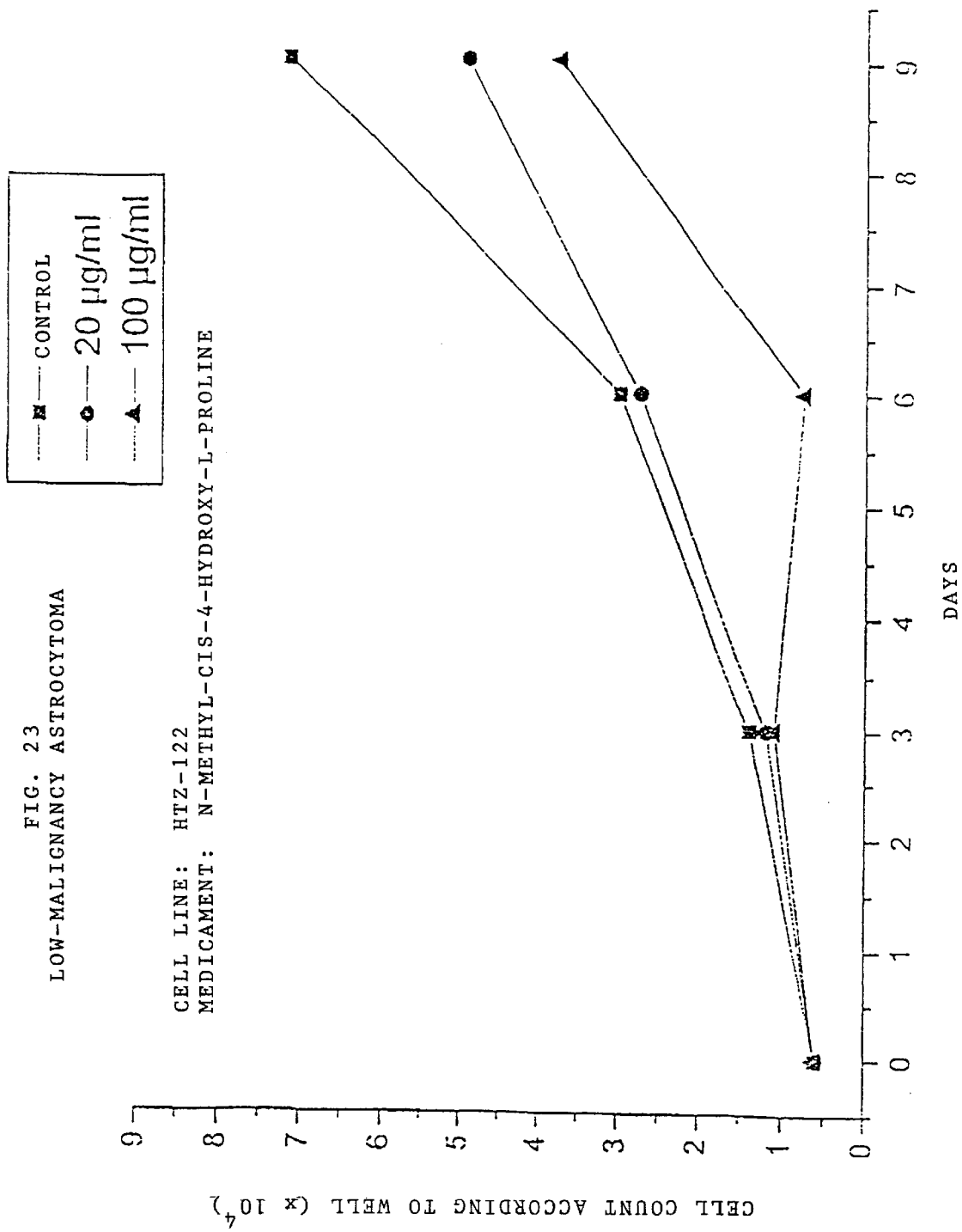
FIG. 23 is a plot of HTZ-122 cell counts for various concentrations of component B.
Figure 24:
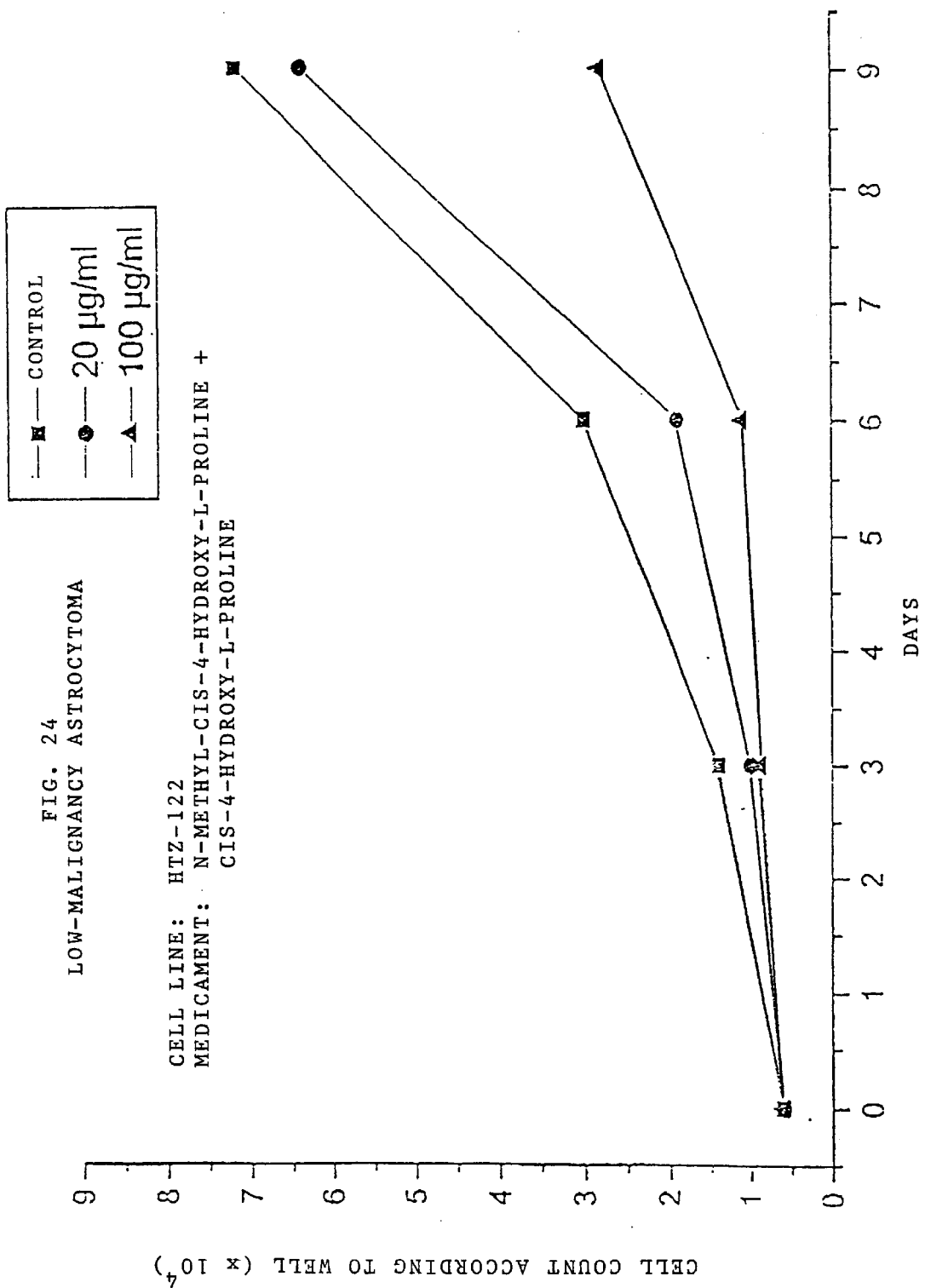
FIG. 24 is a plot of HTZ-122 cell counts for various concentrations of the combination K.

With the brain tumor cell line HTZ 122, the individual components (A) and (B) and the combination (K) all displayed activity, but the combination (K) was the most potent, with an inhibition of c. 66%. This effect was dose-dependent. See FIGS. 22–24.

Figure 25:
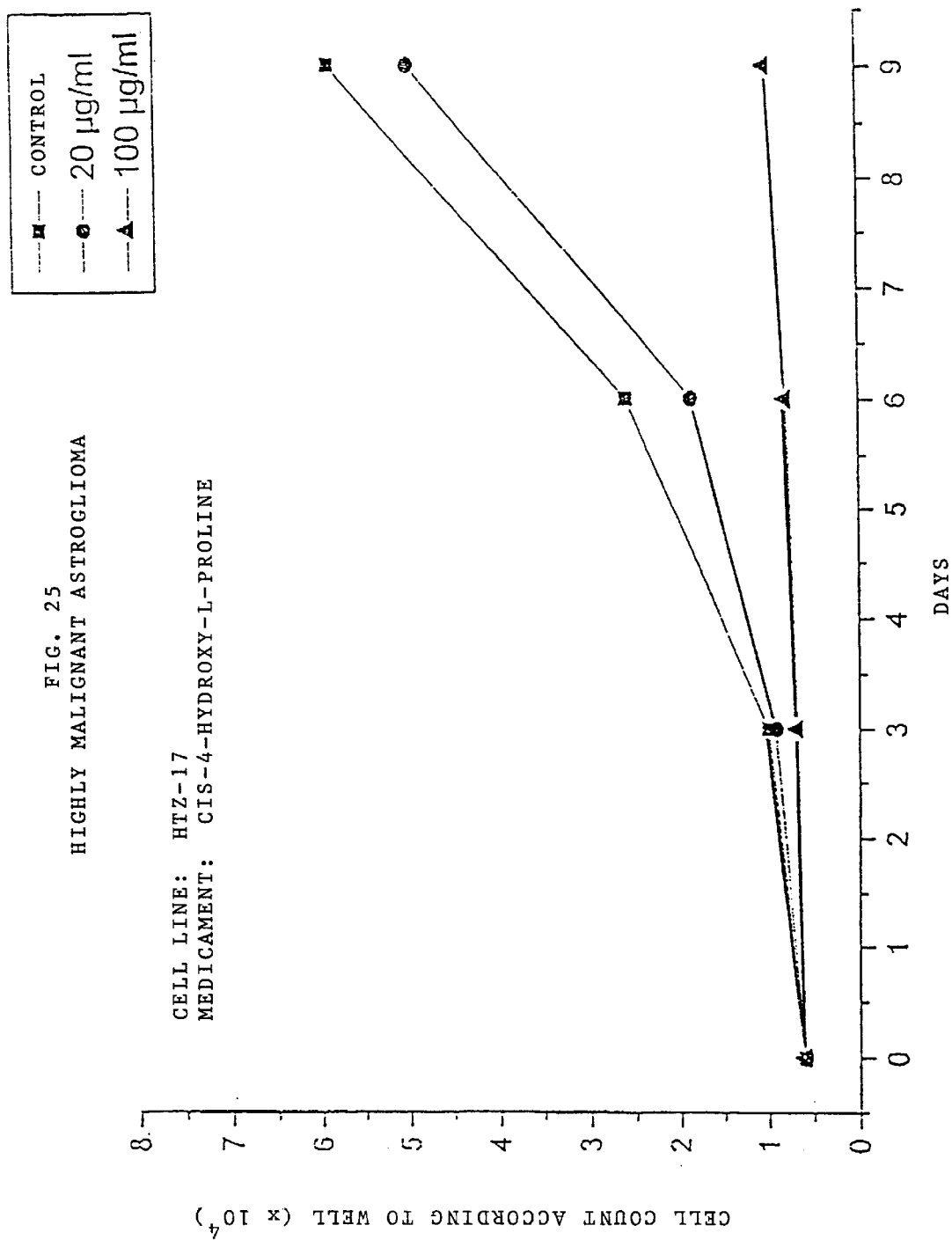
FIG. 25 is a plot of HTZ-17 cell counts for various concentrations of component A.
Figure 26:
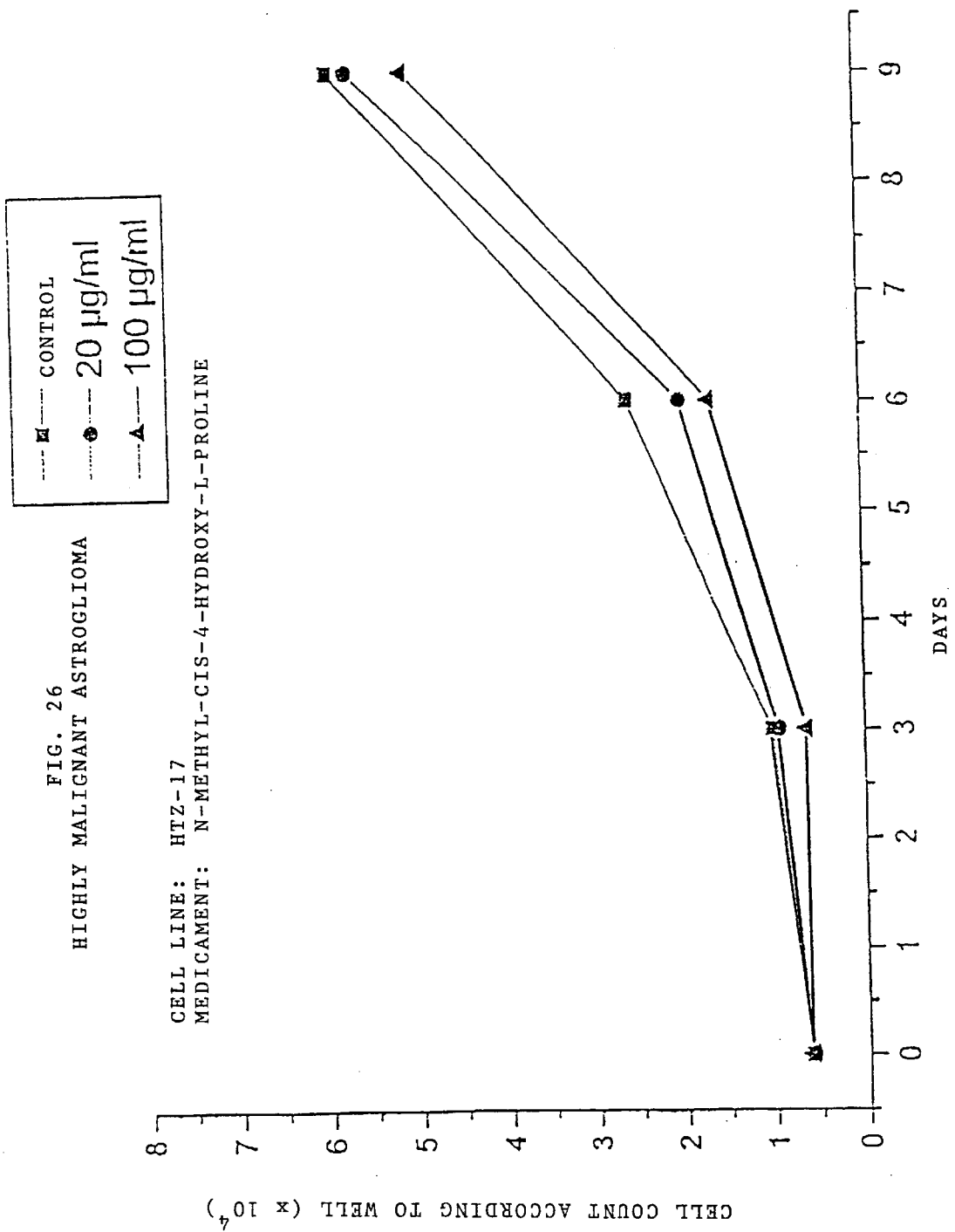
FIG. 26 is a plot of HTZ-17 cell counts for various concentrations of component B.

With the highly malignant brain tumor cell line HTZ 17, the individual component (A) had strong activity, the individual component (B) was only slightly active, and the combination (K) achieved an inhibition of c. 75% See FIGS. 25–27.

Therapeutic Agents and Therapy

Drug formulations containing a combination according to the invention may be prepared according to methods which are per se known. The reader is referred to the book "Remington's pharmaceutical sciences", 1990, 18th Ed., Mack Publishing Co., Easton, Pa., USA, particularly Part 6, "Pharmaceutical preparations and their manufacture". The individual substances can be obtained by chemical synthesis or on the market. The formulations may be prepared for oral or parenteral, particularly intravenous, administration. The customary adjuvants and excipients may be employed. For treating bladder carcinomas, intravesical (transurethral) administration is a possibility; in this case the combination would be administered in the form of a dilute aqueous solution.

The dose will depend on the severity of the disorder. The combination according to the invention may be administered one or more times per day, in individual doses of 0.01–0.1 g/kg body weight.

The inventive therapeutic agents may also contain the components (A) and (B) in the form of pharmaceutically compatible derivatives or precursors. Candidates for these include: alkali salts, earth alkali salts, acid addition salts, esters, amides, acid amides, and ethers, of the described compounds, dehydroproline, and N-alkyl- and/or N-methyl derivatives of dehydroproline, and corresponding keto compounds.

I claim:

1. A combination of cis-4-hydroxy-L-proline (as component A) and N-methyl-cis-4-hydroxy-L-proline (as component B), in a molar ratio which gives rise to synergistic action, for use as therapeutically active agents.

2. A combination according to claim 1, wherein the molar ratio of components (A) and (B) is in the range 10:1 to 1:10.

3. A combination according to claim 1, wherein the molar ratio of components (A) and (B) is 1:1.

4. A therapeutic agent comprised of a combination of cis-4-hydroxy-L-proline (as component A) and N-methyl-cis-4-hydroxy-L-proline (as component B), in a molar ratio which gives rise to synergistic action in the inhibition of cell proliferation of tumor cells sensitive to the combination;
wherein said agent includes a pharmaceutically acceptable carrier.

5. A therapeutic agent according to claim 4, containing components (A) and (B) in a molar ratio in the range 10:1 to 1:10.

6. A therapeutic agent according to claim 4, containing components (A) and (B) in a molar ratio of 1:1.

7. A method of treating tumors, comprising administering to a patient a drug formulation comprising a combination of cis-4-hydroxy-L-proline (as component A) and N-methyl-cis-4-hydroxy-L-proline (as component B), in a molar ratio which gives rise to synergistic action wherein the tumors are sensitive to the combination.

8. The method according to claim 7, wherein the drug formulation is administered to treat bladder carcinoma.

9. The method according to claim 7, wherein the drug formulation is administered to treat hormone-sensitive prostate carcinoma.

10. The method according to claim 7, wherein the drug formulation is administered to treat renal carcinoma.

11. The method according to claim 7, wherein the drug formulation is administered to treat hormone-sensitive mammary carcinoma.

12. The method according to claim 7, wherein the drug formulation is administered to treat fibrosarcoma.

13. The method according to claim 7, wherein the drug formulation is administered to treat brain tumors.

14. The method according to claim 7, wherein the molar ratio of components (A) and (B) is in the range 10:1 to 1:10.

15. The method according to claim 14, wherein the molar ratio of components (A) and (B) is 1:1.

* * * * *